(12) United States Patent
Park et al.

(10) Patent No.: US 10,947,547 B2
(45) Date of Patent: *Mar. 16, 2021

(54) RECOMBINANT MICROORGANISM HAVING ENHANCED 2,3-BUTANEDIOL PRODUCING ABILITY AND METHOD FOR PRODUCING 2,3-BUTANEDIOL USING THE SAME

(71) Applicant: GS CALTEX CORPORATION, Seoul (KR)

(72) Inventors: Jong-Myoung Park, Sejong-si (KR); Hyo-Hak Song, Daejeon (KR); Taek-Ho Yang, Daejeon (KR)

(73) Assignee: GS CALTEX CORPORATION, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/778,467

(22) PCT Filed: Mar. 7, 2014

(86) PCT No.: PCT/KR2014/001920
§ 371 (c)(1),
(2) Date: Sep. 18, 2015

(87) PCT Pub. No.: WO2014/148754
PCT Pub. Date: Sep. 25, 2014

(65) Prior Publication Data
US 2016/0281096 A1 Sep. 29, 2016

(30) Foreign Application Priority Data

Mar. 18, 2013 (KR) .................. 10-2013-0028884
Sep. 26, 2013 (KR) .................. 10-2013-0114791

(51) Int. Cl.
| C12P 7/18 | (2006.01) |
| --- | --- |
| C12N 1/21 | (2006.01) |
| C12N 15/74 | (2006.01) |
| C12N 9/04 | (2006.01) |
| C12N 9/10 | (2006.01) |
| C12N 15/52 | (2006.01) |

(52) U.S. Cl.
CPC .......... *C12N 15/74* (2013.01); *C12N 9/0006* (2013.01); *C12N 9/1029* (2013.01); *C12N 15/52* (2013.01); *C12P 7/18* (2013.01); *C12Y 101/01027* (2013.01); *C12Y 203/01054* (2013.01)

(58) Field of Classification Search
None
See application file for complete search history.

(56) References Cited

U.S. PATENT DOCUMENTS

| 6,280,986 B1 * | 8/2001 | Hespell ............... C12N 9/0006 |
| --- | --- | --- |
| | | 435/161 |
| 10,006,008 B2 * | 6/2018 | Yang .................... C12P 7/18 |
| 2010/0112655 A1 | 5/2010 | Paul |
| 2010/0122655 A1 | 5/2010 | Paul |

FOREIGN PATENT DOCUMENTS

| CN | 101348775 B | * | 7/2011 |
| --- | --- | --- | --- |
| KR | 1020090025902 A | | 3/2009 |
| WO | 9716528 A1 | | 5/1997 |
| WO | 2004043881 A2 | | 5/2004 |
| WO | 2010/037114 A1 | | 4/2010 |
| WO | 2011159853 A1 | | 12/2011 |

OTHER PUBLICATIONS

Park et al., J. Ind. Microbiol. Biotechnol. 40:1057-1066, Jun. 2013.*
Wang et al., Biotechnol. Bioengineer. 109:1610-1621, 2012.*
Machine translation of CN 101348775 B, obtained from espacenet. com, last viewed on Dec. 29, 2016, 20 pages.*
Yang et al., Appl. Microbiol. Biotechnol. 73:1017-1024, 2007.*
Qureshi et al., "Production of 2,3-butanediol by Klebsiella oxytoca", Appl. Microbiol. Biotechnol. 30:440-443, 1989.*
Jung et al., "Deletion of lactate dehydrogenase in Enterobacter aerogenes to enhance 2,3-butanediol production", Appl. Microbiol. Biotechnol. 95:461-469, 2012 (Year: 2012).*
Anvari et al., J. Biomed. Biotechnol. 2011: 636170, 2011, 7 pages (Year: 2011).*
Menzel et al., "Enzymatic evidence for an involvement of pyruvate dehyrogenase in the anaerobic glycerol metabolism of Klbsiella pneumoniae", Journal of Biotechnology, vol. 56, 1997, p. 135-142.
Japanese Office Action dated Sep. 16, 2016 in connection with the counterpart Japanese Patent Application No. 2016-504227, citing the above reference(s).
Xu Yun-Zhen et al., "Metabolism in 1,3-Propanediol Fed-Batch Fermentation by a D-Lactate Deficient Mutant af Klebsiella pneumoniae", Biotechnology and Bioengineering, Dec. 1, 2009, vol. 104, NR. 5, 8 pages.
Lee Sung-Mok et al., "Optimized Production of 2,3-Butanediol by a Lactate Dehydrogenase-deficient Mutant of Klebsiella pneumoniae", Biotechnology and Bioprocess Engineering, Nov. 2013, vol. 18, NR. 6, 6 Pages.
European Search Report dated Mar. 21, 2016 corresponding to European Patent Application No. 147694020 citing the above reference(s).
Jansen et al., "Production of 2,3-Butanediol from D-Xylose by Klebsiella oxytoca ATCC 8724", Biotechnology and Bioengineering, Apr. 1984, pp. 362-369, vol. 26, John Wiley & Sons, Inc.
Jansen et al., "Bioconversion of Pentoses to 2,3-Butanediol by Klebsiella pneumoniae", Adv. Biochem., 1983, pp. 85-99.

(Continued)

*Primary Examiner* — David Steadman
(74) *Attorney, Agent, or Firm* — Hauptman Ham, LLP

(57) ABSTRACT

Disclosed herein is a recombinant microorganism having enhanced 2,3-butanediol producing ability, wherein a pathway for converting pyruvate to acetyl-CoA, a pathway for converting pyruvate to formic acid, or a pathway for converting pyruvate to lactate is inhibited in a microorganism having acetyl-CoA and lactate biosynthetic pathways.

8 Claims, 13 Drawing Sheets

Specification includes a Sequence Listing.

(56) References Cited

OTHER PUBLICATIONS

Ji et al., "Enhanced 2,3-butanediol production by altering the mixed acid fermentation pathway in Klebsiella oxytoca", Biotechnol Lett, 2008, pp. 731-734, Springer.

E. Celinska et al., "Biotechnological production of 2,3-butanediol-Current state and prospects", Biotechnology Advances, May 2, 2009, pp. 715-725, vol. 27, Elsevier Inc.

Ji et al., "Microbial 2,3-butanediol production: A state-of-the-art review", Biotechnology Advances, Jan. 24, 2011, pp. 351-364, vol. 29, Elsevier Inc.

Chandel et al., "Biotechnological Applications of Hemicellulosic Derived Sugars: State-of-the-Art", Sustainable Biotechnology, 2010, pp. 63-81, Springer Science+Business Media B.V.

Ji et al., "Enhanced 2,3-butanediol production by Klebsiella oxytoca using a two-stage agitation speed control strategy", Bioresource Technology, Mar. 17, 2009, pp. 3410-3414, vol. 100, Elsevier Ltd.

Nakashimada et al., "Enhanced 2,3-Butanediol Production by Addition of Acetic Acid in Paenibacillus polymyxa", Journal of Bioscience and Bioengineering, 2000, pp. 661-664, vol. 90, No. 6.

Nakashimada et al., "Optimization of dilution rate, pH and oxygen supply on optical purity of 2, 3-butanediol produced by Paenibacillus polymyxa in chemostat culture", Biotechnology Letters, Dec. 1998, pp. 1133-1138, vol. 20, No. 12, Chapman & Hall.

Ma et al., "Enhanced 2,3-butanediol production by Klebsiella pneumoniae SDM", Biotechnological products and process engineering, Oct. 24, 2008, pp. 49-57, Springer.

Nielsen et al., "Metabolic engineering of acetoin and meso-2,3-butanediol biosynthesis in *E. coli*", Biotechnology Journal, 2010, pp. 274-284, vol. 5, Wiley-VCH Verlag GmbH & Co. KGaA, Weinheim.

Wu et al., "Improved Succinic Acid Production in the Anaerobic Culture of an *Escherichia coli* pflB ldhA Double Mutant as a Result of Enhanced Anaplerotic Activities in the Preceding Aerobic Culture", Applied and Environmental Microbiology, Dec. 2007, pp. 7837-7843, vol. 73, No. 24, American Society for Microbiology.

Office Action dated Dec. 7, 2016 from SIPO in connection with the counterpart Chinese Patent Application No. 201480016956.9, citing the above reference(s).

Canadian Office Action dated May 1, 2017 for Canadian Patent Application No. 2,907,646.

\* cited by examiner

RECOMBINANT MICROORGANISM HAVING ENHANCED 2,3-BUTANEDIOL PRODUCING ABILITY AND METHOD FOR PRODUCING 2,3-BUTANEDIOL USING THE SAME

CROSS REFERENCE TO RELATED APPLICATION

This application claims the priority of Korean Patent Application No. 10-2013-0028884, filed Mar. 18, 2013 and Korean Patent Application No. 10-2013-0114791 filed Sep. 26, 2013 in the KIPO (Korean Intellectual Property Office). Further, this application is the National Phase application of International Application No. PCT/KR2014/001920 filed Mar. 7, 2014, which designates the United States and was published in Korean.

TECHNICAL FIELD

The present invention relates to a recombinant microorganism having enhanced 2,3-butanediol producing ability, and a method for producing 2,3-butanediol using the same.

BACKGROUND ART 2,3-butanediol ($CH_3CHOHCHOHCH_3$) which is one of alcohols having four carbons and two hydroxyl groups (—OH) is capable of being converted to a chemical catalyst with 1,3-Butadiene which is a raw material used in a manufacturing process of synthetic rubber and methyl ethyl ketone (MEK) used as a fuel additive and a solvent (Ji et al., Biotechnol. Adv., 29: 351, 2011). In addition, 2,3-butanediol is applicable as an octane booster by being mixed with gasoline, which is a significantly important intermediate in fuel industries (Celinska et al., Biotechnol. Adv., 27: 715, 2009).

2,3-butanediol is capable of being produced by a chemical synthesis process and a microbial fermentation process. However, since production cost for 2,3-butanediol through the above-described processes is significantly high, industrial-scale production of 2,3-butanediol is not achieved. Meanwhile, in accordance with a rapid increase in price of fossil raw materials and reinforcement of regulation on international environmental pollution, together with the recent and fast development of a technology of producing 2,3-butanediol through a microorganism fermentation process, importance of an interest in production of bio-based 2,3-butanediol through microorganism fermentation and research and development thereof have been increased.

A method for producing the bio-based 2,3-butanediol is to convert renewable biomass to 2,3-butanediol through fermentation of microorganism having 2,3-butanediol producing ability. 2,3-butanediol is produced by various kinds of microorganisms such as *Klebsiella* species, *Enterobacter* species, *Bacillus* species, *Serratia* species, and the like (Maddox IS, Biotechnol., 6: 269, 1996). In particular, *Klebsiella pneumoniae* (*K. pneumoniae*), *Klebsiella oxytoca* (*K. oxytoca*), and *Paenibacillus polymyxa* produce a relatively large amount of 2,3-butanediol. Particularly, *Klebsiella pneumoniae* (*K. pneumoniae*) and *Klebsiella oxytoca* (*K. oxytoca*) have advantages in that culturing is easily performed, a growth rate is rapid, and 2,3-butanediol is capable of being produced from various kinds of biomasses including lignocellulosic-derived pentose (Ji et al., Biotechnol. Adv., 29: 351, 2011; Chandel et al., Sustainable Biotechnol., 63, 2010; Jansen et al., Biotechnol. Bioeng., 26: 362, 1984; Jansen et al., Adv. Biochem. Eng., 27: 85, 1983).

Research on production of the bio-based 2,3-butanediol through the microorganism fermentation process has been conducted according to two fields divided into a field of optimization (temperature, pH, dissolved oxygen, and the like) of a fermentation process and a field of microorganism development (microorganism discovery, understanding of physiological characteristics, mutation, genetic engineering, and the like). In the field of optimization of the fermentation process, various conditions such as temperature, pH, concentration of dissolved oxygen, and the like for effectively producing 2,3-butanediol were identified (Ji et al., Bioresour. Technol., 100: 3410, 2009; Nakashimada et al., J. Biosci. Bioeng., 90: 661, 2000; Nakashimada et al., Biotechnol. Lett., 20: 1133, 1998). However, production of 2,3-butanediol through the microorganism fermentation process under the above-described conditions still has difficulty in being directly applied to commercial processes due to low productivity and yield. In addition, the production has a disadvantage in that various by-products such as organic acids including lactic acid, alcohols including ethanol, and the like, also occur, together with 2,3-butanediol in the fermentation process. The occurrence of by-products reduces yield of 2,3-butanediol for biomass, and requires enormous cost for separation and purification in a process of recovering 2,3-butanediol from a culture fluid.

Accordingly, research on the development of microorganisms associated with the production of 2,3-butanediol has mainly progressed by reducing the by-products. As a representative method, Ji et al., achieved success by partially inhibiting occurrence of organic acids which are by-products, by exposing UV to a wild-type *Klebsiella oxytoca* strain as one of the physical chemical mutagenesis methods (Ji et al., Biotechnol. Lett., 30: 731, 2008). In addition, There is an attempt to improve the production of 2,3-butanediol by applying an ion injection (ion beam) method to a *Klebsiella pneumoniae* strain to increase a consumption speed of biomass (Ma et al., Appl. Microbiol. Biotechnol., 82: 49, 2009). However, the above-developed strains are still insufficient to be directly applied to commercial processes in view of productivity, final concentration, and yield of 2,3-butanediol.

Therefore, the present inventors studied a recombinant microorganism not only having high productivity, high concentration, and high yield of 2,3-butanediol, but also having high selectivity of 2,3-butanediol, which generates less by-products, and found that a recombinant microorganism from which specific genes are deleted has a small amount of by-products while simultaneously having high selectivity and high productivity of 2,3-butanediol, and accordingly, completed the present invention.

DISCLOSURE

Technical Problem

An object of the present invention is to provide a recombinant microorganism having enhanced 2,3-butanediol producing ability, and a method for producing 2,3-butanediol using the same.

Technical Solution

In order to achieve the object of the present invention, according to an exemplary embodiment of the present invention, there is provided a recombinant microorganism having enhanced 2,3-butanediol producing ability, wherein a pathway for converting pyruvate to acetyl-CoA, a pathway for converting pyruvate to formic acid, or a pathway for converting pyruvate to lactate is inhibited in a microorganism having acetyl-CoA and lactate biosynthetic pathways.

According to another exemplary embodiment of the present invention, there is provided a method for producing 2,3-butanediol, the method including:

culturing the recombinant microorganism as described above; and recovering 2,3-butanediol from the cultured recombinant microorganism.

Advantageous Effects

The recombinant microorganism according to the present invention may produce 2,3-butanediol with high selectivity and concentration.

DESCRIPTION OF THE EXEMPLARY EMBODIMENTS

The present invention relates to:

a recombinant microorganism having enhanced 2,3-butanediol producing ability, wherein a pathway for converting pyruvate to acetyl-CoA, a pathway for converting pyruvate to formic acid, or a pathway for converting pyruvate to lactate is inhibited in a microorganism having acetyl-CoA and lactate biosynthetic pathways.

In addition, the present invention relates to:

a method for producing 2,3-butanediol, the method including: culturing the recombinant microorganism of the present invention;

and recovering 2,3-butanediol from the cultured recombinant microorganism.

Hereinafter, the present invention is described in detail.

Recombinant Microorganism Having Enhanced Producing Ability of 2,3-butanediol

The recombinant microorganism of the present invention is a recombinant microorganism having enhanced 2,3-butanediol producing ability, wherein the pathway for converting pyruvate to acetyl-CoA, the pathway for converting pyruvate to formic acid, or the pathway for converting pyruvate to lactate is inhibited in a microorganism having acetyl-CoA and lactate biosynthetic pathways.

In addition, the recombinant microorganism of the present invention is a recombinant microorganism from which a gene encoding alcohol dehydrogenation enzyme (aldehyde/alcohol dehydrogenase), that is, adhE, is not deleted.

Figure 1:
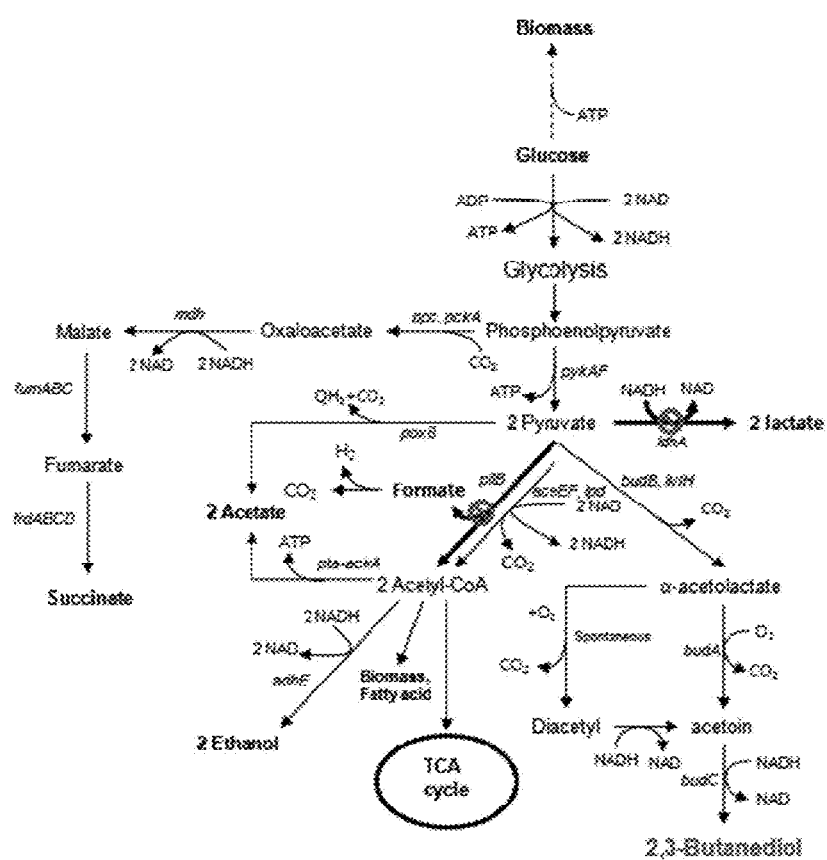
FIG. 1 is a diagram illustrating a pathway in which 2,3-butanediol is synthesized in a *Klebsiella* strain.

Preferably, as illustrated in FIG. 1, the recombinant microorganism of the present invention is a recombinant microorganism in which the pathway for converting pyruvate to acetyl-CoA, the pathway for converting pyruvate to formic acid, or the pathway for converting pyruvate to lactate is inhibited while having acetyl-CoA and lactate biosynthetic pathways.

In addition, the recombinant microorganism of the present invention has high selectivity, yield, concentration, and productivity of 2,3-butanediol. That is, in the recombinant microorganism of the present invention, selectivity of 2,3-butanediol is 70% or more, preferably, 80% or more, and a yield of 2,3-butanediol is 0.35 g/g or more based on batch culture or fed-batch culture. Further, due to the recombination, the recombinant microorganism of the present invention better inhibits a producing ability of formic acid, acetic acid, or ethanol as compared to a wild-type microorganism.

Biosynthetic Pathway of Acetyl-CoA

A biosynthetic pathway of acetyl-CoA of the present invention means a pathway in which acetyl-CoA is synthesized from a specific metabolite in a microorganism. The biosynthetic pathway of acetyl-CoA of the present invention may be a pathway for synthesizing acetyl-CoA from pyruvate, and the like.

Biosynthetic Pathway of Lactate

A biosynthetic pathway of lactate of the present invention means a pathway in which lactate is synthesized from a specific metabolite in a microorganism. The biosynthetic pathway of lactate of the present invention may be a pathway for synthesizing lactate from pyruvate, and the like.

Microorganism Having Acetyl-CoA and Lactate Biosynthetic Pathways

The microorganism having the biosynthetic pathway of acetyl-CoA and the biosynthetic pathway of lactate of the present invention is not specifically limited as long as it has the above-described biosynthetic pathways. In addition, the microorganism of the present invention may be a microorganism having the acetyl-CoA biosynthetic pathway and the lactate biosynthetic pathway in a wild-type or a recombinant microorganism having the acetyl-CoA biosynthetic pathway and the lactate biosynthetic pathway by gene recombination.

For example, the microorganisms of the present invention may be included in *Klebsiella* genus, *Bacillus* genus, *Serratia* genus, or *Enterobacter* genus, preferably, *Klebsiella oxytoca* (*K. oxytoca*), *Klebsiella pneumoniae* (*K. pneumoniae*), and the like, and the most preferably, *Klebsiella oxytoca* (*K. oxytoca*).

Inhibition of Pathway for Converting Pyruvate to Acetyl-CoA

Pyruvate-formate lyase controls conversion of pyruvate to acetyl-CoA. A pathway for converting pyruvate to acetyl-CoA may be inhibited by inhibiting the pyruvate-formate lyase. The inhibition of the pyruvate-formate lyase may be achieved by inhibition of expression of the pyruvate-formate lyase, inhibition of enzyme activity of the pyruvate-formate lyase, and the like. For example, the pyruvate-formate lyase may be inhibited by selecting appropriate methods by a person skilled in the art, the appropriate methods such as deletion of pflB which is a gene encoding the pyruvate-formate lyase, development of mutants in the gene (a mutant inhibiting expression of a normal gene by mutating, substituting or deleting partial bases from the gene, or by introducing partial bases into the gene), regulation of gene expression in a transcription process or a translation process, and the like.

Inhibition of Pathway for Converting Pyruvate to Formic Acid

Pyruvate-formate lyase controls conversion of pyruvate to formic acid. A pathway for converting pyruvate to formic acid may be inhibited by inhibiting the pyruvate-formate lyase. The inhibition of the pyruvate-formate lyase may be achieved by inhibition of expression of the pyruvate-formate lyase, inhibition of enzyme activity of the pyruvate-formate lyase, and the like. For example, the pyruvate-formate lyase may be inhibited by selecting appropriate methods by a person skilled in the art, the appropriate methods such as deletion of pflB which is a gene encoding the pyruvate-formate lyase, development of mutants in the gene (a mutant inhibiting expression of a normal gene by mutating, substituting or deleting partial bases from the gene, or by introducing partial bases into the gene), regulation of gene expression in a transcription process or a translation process, and the like.

Inhibition of Pathway for Converting Pyruvate to Lactate

Lactate dehydrogenase controls conversion of pyruvate to lactate A pathway for converting pyruvate to lactate may be inhibited by inhibiting the lactate dehydrogenase. The inhibition of the lactate dehydrogenase may be achieved by inhibition of expression of the lactate dehydrogenase, inhibition of enzyme activity of the lactate dehydrogenase, and the like. For example, the lactate dehydrogenase may be inhibited by selecting appropriate methods by a person skilled in the art, the appropriate methods such as deletion of ldha which is a gene encoding the lactate dehydrogenase, development of mutants in the gene (a mutant inhibiting expression of a normal gene by mutating, substituting or deleting partial bases from the gene, or by introducing partial bases into the gene), regulation of gene expression in a transcription process or a translation process, and the like.

Alcohol Dehydrogenation Enzyme

An alcohol dehydrogenation enzyme (aldehyde/alcohol dehydrogenase) controls a pathway for converting acetyl-CoA to ethanol. Accordingly, there is a case of promoting an increase of production of 2,3-butanediol by deleting adhE which is a gene encoding alcohol dehydrogenation enzyme to inhibit occurrence of ethanol (Ji et al., Appl. Microbiol. Biotechnol., 85: 1751, 2010). However, in the recombinant microorganism of the present invention, when adhE is additionally deleted, a production amount, selectivity, and productivity of 2,3-butanediol are remarkably decreased. Accordingly, adhE which is a gene encoding the alcohol dehydrogenation enzyme is not deleted in the present invention.

Method for Producing 2,3-Butanediol

A method for producing 2,3-butanediol of the present invention includes culturing the recombinant microorganism of the present invention; and recovering 2,3-butanediol from the cultured recombinant microorganism.

The culturing is performed under aerobic condition, preferably, microaerobic condition. For example, the culturing is performed while supplying oxygen, that is, air during the culturing, and specifically, the supplying of the oxygen may be performed by agitating. Preferably, the culturing is performed while agitating at an agitation speed of 450 rpm or less, more preferably, 50 to 450 rpm, and still more preferably, 150 to 450 rpm.

Preferably, the culturing may control productivity of 2,3-butanediol by controlling an oxygen supply amount. As a method for controlling the oxygen supply amount during the culturing, for example, the culturing of the present invention may be performed while agitating, and the culturing may control productivity of 2,3-butanediol by controlling the agitation speed during the culture. For example, when a concentration of acetoin is increased to be 5 g/L or more, preferably, 10 g/L or more, an agitation speed may be decreased, which increases concentration and productivity of 2,3-butanediol and inhibits occurrence of by-products.

BEST MODE

Various advantages and features of the present invention and methods accomplishing thereof will become apparent from the following description of embodiments with reference to the accompanying drawings. However, the present invention is not limited to exemplary embodiment disclosed herein but will be implemented in various forms. The exemplary embodiments are provided by way of example only so that a person of ordinary skilled in the art can fully understand the disclosures of the present invention and the scope of the present invention. Therefore, the present invention will be defined only by the scope of the appended claims.

Material and Method 2,3-butanediol concentration (g/L): Amount of 2,3-butanediol to be produced per unit volume 2,3-butanediol yield (g/g): Production amount (g) of 2,3-butanediol/carbon source (g)×100

2,3-butanediol productivity (g/L/h): Amount of 2,3-butanediol to be produced per unit time and unit volume Selectivity (%) of 2,3-butanediol: Production amount (g) of 2,3-butanediol/(production amounts (g) of 2,3-butanediol, ethanol, acetoin, succinic acid, lactate formate, and acetic acid)×100

<Experimental Example 1> Production of Recombinant Microorganism

In order to inactivate a target gene of *Klebsiella oxytoca* produced with a DNA fragment including a homologous region of the target gene, a recombinant mechanism of bacteria was used, and the homologous region of the gene to be removed was amplified by PCR. Then, the corresponding DNA fragment including the homologous region was transferred to bacteria, and then, the target gene was removed by the recombinant mechanism by recombinase between the homologous region of the gene in the DNA fragment and a gene in chromosome of *Klebsiella oxytoca*.

First, in order to perform cloning of lactate dehydrogenase of *Klebsiella oxytoca*, a homologous region 1 (SEQ ID NO: 2) of ldhA (SEQ ID NO: 1) which is a target gene was amplified with primers of SEQ ID NOs: 3 and 4 by PCR. In addition, a homologous region 2 (SEQ ID NO: 5) thereof was amplified with primers of SEQ ID NOs: 6 and 7 by PCR. Then, both of the homologous regions 1 and 2 were simultaneously used as a template and amplified by PCR, thereby completing a DNA fragment (SEQ ID NO: 8) including the homologous regions 1 and 2.

Meanwhile, in order to perform cloning of a homologous region of pyruvate-formate lyase of *Klebsiella oxytoca*, a homologous region 1 (SEQ ID NO: 10) of pflB (SEQ ID NO: 9) which is a target gene was amplified with primers of SEQ ID NOs: 11 and 12 by PCR. In addition, a homologous region 2 (SEQ ID NO: 13) thereof was amplified with primers of SEQ ID NOs: 14 and 15 by PCR. Then, both of the homologous regions 1 and 2 were simultaneously used as a template and amplified by PCR, thereby completing a DNA fragment (SEQ ID NO: 16) including the homologous regions 1 and 2 (Table 1). In order to increase recombination probability of the target gene, the completed DNA fragment may include an anti-biotic resistance gene, and the like. Further, the DNA fragment may include a sacB gene encoding a levansucrase enzyme, in order to remove the recombinant anti-biotic resistance gene in chromosome.

TABLE 1

| SEQ ID NO. | SEQUENCES |
|---|---|
| 1 | ATGAAAATCGCTGTGTATAGTACAAAACAGTACGACAAGAAGTATCTGCAGGATGTTAATGATG<br>CATATGGCTTTGAACTGGAGTTTTTTGACTTCCTGCTAACCGAAAAAACCGCCAAAACCGCCA<br>ACGGCTGTGAAGCGGTGTGTATCTTCGTAAACGATGACGGTAGCCGCCCGGTACTTGAAGAA<br>CTGAAAGCCCACGGCGTGCAGTACATCGCGCTGCGCTGCGCGGGGTTCAACAACGTTGACC<br>TCGATGCCGCCAAAGAGCTGGGCCTGGGGGTGGTGCGCGTCCCGGCCTACTCGCCGGAAG<br>CGGTCGCTGAGCACGCGATACGGCATGATGATGTCGCTGAACCGCCGCATTCACCGTGCCTA<br>TCAGCGCACCCGCGACGCGAACTTCTCTCTGGAAGGGCTGACCGGTTTCACCATGCACGGT<br>AAAACCGCCGGCGTTATTGGCACCGGTAAAATCGGCGTCGCCGCGCTGCGCATTCTTAAAG<br>GCTTCGGTATGCGTCTGCTGGCGTTTGATCCCTACCCAAGCGCCGCCGCGCTGGATATGGG<br>CGTGGAGTATGTCGATCTTGAAACCCTGTACGGGAGTCCGATGTTATCTCACTGCACTGCC<br>CACTGACCGATGAAAACTACCATTTGCTGAACCATGCCGCGTTCGATCGCATGAAAGACGGG<br>GTGATGATCATCAACACCAGCCGCGGCGCGCTCATCGATTCGCAGGCAGCGATCGACGCCC<br>TGAAGCATCAGAAAATTGGCGCGCTGGGGATGGACGTGTATGAGAACGAACGCGATCTGTTC<br>TTTGAAGATAAGTCTAATGACGTGATTCAGGATGATGTGTTCCGCCGTCTCTCCGCCTGCCAT<br>AACGTCCTGTTTACCGGTCACCAGGCGTTTCTGACCGCGGAAGCGTTGATCAGCATTTCGCA<br>AACCACCCTCGACAACCTGCGTCAAGTGGATGCAGGCGAAACCTGTCCTAACGCACTGGTCT<br>GA |
| 2 | ATGACGTTCGCTAAATCCTGCGCCGTCATCTCGCTGCTGATCCCGGGCACCTCCGGGCTACT<br>GCTGTTCGGCACCCTGGCATCGGCCAGCCCGGGACATTTCCTGTTAATGTGGATGAGCGCC<br>AGCCTCGGCGCTATCGGCGGATTCTGGCTCTCGTGGCTGACGGGCTACCGCTACCGGTACC<br>ATCTGCATCGTATCCGGTGGCTTAATGCCGAACGCCTCGGCTCGCGGCCAGTTGTTCCTGCGC<br>CGCCACGGCGCGTGGGCAGTCTTTTTTAGCCGCTTTCTCTCTCCGCTGCGCGCCACCGTGC<br>CGCTGGTAACCGGCGCCAGCGGCCACCTCTCTCTGGCAGTTTCAGCTCGCCAACGTCAGCTC<br>CGGGCTGCTCTGGCCGCTGATCCTGCTGGCGCCAGGCGCGTTAAGCCTCAGCTTTTGATGA<br>AAGGTATTGTCTTTTAAAGAGATTTCTTAACACCGCGATATGCTCTAGAATTATTACTATAACCT<br>GCTGATTAAACTAGTTTTTAACATTTGTAAGATTATTTTAATTATGCTACCGTGACGGTATTATCA<br>CTGGAGAAAAGTCTTTTTTCCTTGCCCTTTTGTGC |
| 3 | Ko_ldhA_FP1 - CACGGATCCATGACGTTCGCTAAATCCTGC |
| 4 | Ko_ldhA_RP1 - GCACAAAAGGGCAAGGAAAAAAGACTTTTCTCCAGTGATA |
| 5 | TATCACTGGAGAAAAGTCTTTTTTCCTTGCCCTTTTGTGCTCCCCCTTCGCGGGGGGCACATT<br>CAGATAATCCCCACAGAAATTGCCTGCGATAAAGTTACAATCCCTTCATTTATTAATACGATAA<br>ATATTTATGGAGATTAAATGAACAAGTATGCTGCGCTGCTGGCGGTGGGAATGTTGCTATCGG<br>GCTGCGTTTATAACAGCAAGGTGTCGACCAGAGCGGAACAGCTTCAGCACCACCGTTTTGTG<br>CTGACCAGCGTTAACGGGCAGCCGCTGAATGCCGCGGATAAGCCGCAGGAGCTGAGCTTC<br>GGCGAAAAGATGCCCATTACGGGCAAGATGTCTGTTTCAGGTAATATGTGCAACCGCTTCAG<br>CGGCACGGGCAAAGTCTCTGACGGCGAGCTGAAGGTTGAAGAGCTGGCAATGACCCGCATG<br>CTCTGCACGGACTCGCAGCTTAACGCCCTGGACGCCACGCTGAGCAAAATGCTGCGCGAAG<br>GCGCGCAGGTCGACCTGACGGAAACGCAGCTAACGCTGGCGACCGCCGACCAGACGCTGG<br>TGTATAAGCTCGCCGACCTGATGAATTAATAATTA |
| 6 | Ko_ldhA_FP2 - TATCACTGGAGAAAAGTCTTTTTTCCTTGCCCTTTTGTGC |
| 7 | Ko_ldhA_RP2 - CCTGCGGCCGCTAATTATTAATTCATCAGGTC |
| 8 | ATGACGTTCGCTAAATCCTGCGCCGTCATCTCGCTGCTGATCCCGGGCACCTCCGGGCTACT<br>GCTGTTCGGCACCCTGGCATCGGCCAGCCCGGGACATTTCCTGTTAATGTGGATGAGCGCC<br>AGCCTCGGCGCTATCGGCGGATTCTGGCTCTCGTGGCTGACGGGCTACCGCTACCGGTACC<br>ATCTGCATCGTATCCGCTGGCTTAATGCCGAACGCCTCGCTCGCGGCCAGTTGTTCCTGCGC<br>CGCCACGGCGCGTGGGCAGTCTTTTTTAGCCGCTTTCTCTCTCCGCTTGCGCGCCACCGTGC<br>CGCTGGTAACCGGCGCCAGCGGCACCTCTCTCTGGCAGTTTCAGCTCGCCAACGTCAGCTC<br>CGGGCTGCTCTGGCCGCTGATCCTGCTGGCGCCAGGCGCGTTAAGCCTCAGCTTTTGATGA<br>AAGGTATTGTCTTTTAAAGAGATTTCTTAACACCGCGATATGCTCTAGAATTATTACTATAACCT<br>GCTGATTAAACTAGTTTTTAACATTTGTAAGATTATTTTAATTATGCTACCGTGACGGTATTATCA<br>CTGGAGAAAAGTCTTTTTTCCTTGCCCTTTTGTGCTCCCCCTTCGCGGGGGGCACATTCAGAT |

TABLE 1-continued

| SEQ ID NO. | SEQUENCES |
|---|---|
|  | AATCCCCACAGAAATTGCCTGCGATAAAGTTACAATCCCTTCATTTATTAATACGATAAATATTT<br>ATGGAGATTAAATGAACAAGTATGCTGCGCTGCTGGCGGTGGGAATGTTGCTATCGGGCTGC<br>GTTTATAACAGCAAGGTGTCGACCAGAGCGGAACAGCTTCAGCACCACCGTTTTGTGCTGAC<br>CAGCGTTAACGGGCAGCCGCTGAATGCCGCGGATAAGCCGCAGGAGCTGAGCTTCGGCGA<br>AAAGATGCCCATTACGGGCAAGATGTCTGTTTCAGGTAATATGTGCAACCGCTTCAGCGGCA<br>CGGGCAAAGTCTCTGACGGCGAGCTGAAGGTTGAAGAGCTGGCAATGACCCGCATGCTCTG<br>CACGGACTCGCAGCTTAACGCCCTGGACGCCACGCTGAGCAAAATGCTGCGCGAAGGCGC<br>GCAGGTCGACCTGACGGAAACGCAGCTAACGCTGGCGACCGCCGACCAGACGCTGGTGTA<br>TAAGCTCGCCGACCTGATGAATTAATAATTA |
| 9 | ATGTCCGAGCTTAATGAAAAGTTAGCCACAGCCTGGGAAGGTTTTGCGAAAGGTGACTGGCA<br>GAACGAAGTCAACGTCCGCGACTTCATCCAGAAAAACTATACCCCGTACGAAGGTGACGAGT<br>CCTTCCTGGCTGGCGCAACTGACGCGACCACCAAGCTGTGGGACACCGTAATGGAAGGCGT<br>TAAACAGGAAAACCGCACTCACGCGCCTGTTGATTTTGATACTTCCCTTGCATCCACCATCAC<br>TTCTCATGACGCTGGCTACATCGAGAAAGGTCTCGAGAAAATCGTTGGTCTGCAGACTGAAG<br>CTCCGCTGAAACGCGCGATTATCCCGTTCGGCGGCATCAAAATGGTCGAAGGTTCCTGCAAA<br>GCGTACGATCGCGAGCTGGACCCGATGCTGAAGAAAATCTTCACTGAATACCGTAAAACTCA<br>CAACCAGGGCGTGTTTGACGTTTACACCAAAGACATCCTGAACTGCCGTAAATCTGGTGTTCT<br>GACCGGTCTGCCGGATGCCTATGGCCGTGGTCGTATCATCGGTGACTACCGTCGCGTTGCG<br>CTGTACGGTATCGACTTCCTGATGAAAGACAAATACGCTCAGTTCGTTTCTCTGCAAGAGAAA<br>CTGGAAAACGGCGAAGATCTGGAAGCAACCATCCGTCTGCGCGAAGAAATCTCTGAACAGCA<br>CCGCGCGCTGGGTCAGATCAAAGAAATGGCGGCTAAATATGGCTGCGATATCTCTGGTCCTG<br>CTACCACCGCTCAGGAAGCTATCCAGTGGACCTACTTCGGTTACCTGGCTGCCGTAAAATCT<br>CAGAACGGCGCGGCAATGTCCTTCGGTCGTACCTCCAGCTTCCTGGACATCTTCATCGAACG<br>TGACCTGAAAGCCGGTAAAATCACCGAGCAAGACGCACAGGAAATGATTGACCACCTGGTCA<br>TGAAACTGCGTATGGTTCGTTTCCTGCGTACCCCTGAATATGATGAACTGTTCTCTGGCGACC<br>CGATCTGGGCAACAGAATCTATCGGCGGTATGGGCGTTGACGGCCGTACTCTGGTCACCAA<br>AAACAGCTTCCGTTTCCTGAACACCCTGTACACCATGGGGCCGTCTCCGGAGCCGAACATCA<br>CCATTCTGTGGTCTGAAAAACTGCCGCTGAGCTTCAAAAAATACGCCGCGAAAGTGTCCATC<br>GATACCTCTTCTCTGCAGTACGAGAACGATGACCTGATGCGTCCTGACTTCAACAACGATGAC<br>TACGCTATCGCTTGCTGCGTAAGCCCGATGGTTGTTGGTAAGCAAATGCAGTTCTTCGGCGC<br>GCGTGCTAACCTGGCGAAAACCATGCTGTACGCAATAACGGCGGCGTTGATGAAAAACTGA<br>AAATGCAGGTTGGTCCTAAATCTGAACCGATCAAAGGCGACGTTCTGAACTTCGACGAAGTGA<br>TGGACCGCATGGATCACTTCATGGACTGGCTGGCTAAACAGTACGTCACTGCGCTGAACATC<br>ATCCACTACATGCACGACAAGTACAGCTACGAAGCTTCCCTGATGGCGCTGCACGACCGTGA<br>TGTTTATCCGCACCATGGCATGTGGTATCGCAGGTCTTTCCGTTGCGGCTGACTCCCTGTCTG<br>CAATCAAATATGCGAAAGTTAAACCGATTCGTGACGAAAACGGTCTGGCTGTCGACTTCGAAA<br>TCGAAGGCGAATACCCCGCAGTTTGGTAACAACGACTCTCGCGTCGATGATATGGCCGTTGAC<br>CTGGTTGAACGTTTCATGAAGAAAATTCAGAAACTGCACACCTACCGCAACGCTATCCCGACT<br>CAGTCCGTTCTGACCATCACCTCTAACGTTGTGTATGGTAAGAAAACCGGCAACACCCCTGA<br>CGGTCGTCGCGCTGGCGCTCCGTTCGGACCAGGTGCTAACCCGATGCACGGCCGTGACCA<br>GAAAGGCGCTGTTGCCTCTCTGACCTCCGTTGCAAAACTGCCGTTTGCTTACGCGAAAGATG<br>GTATTTCTTACACCTTCTCTATCGTGCCGAACGCGCTGGGTAAAGACGACGAAGTTCGTAAAA<br>CTAACCTCGCCGGCCTGATGGATGGTTACTTCCACCACGAAGCGTCCATCGAAGGCGGTCA<br>GCATCTGAACGTCAACGTTATGAACCGCGAAATGCTGCTCGACGCGATGGAAAACCCGGAAA<br>AATATCCGCAGCTGACCATCCGCGTATCCGGCTACGCAGTACGTTTTAACTCCCTGACTAAAG<br>AACAGCAGCAGGACGTTATTACTCGTACCTTCACTCAGACCATGTAA |
| 10 | GGGTCAACTGGCGAAAAACTGGCTCAACGTCTATGTTGGTAACCTGATTGGTTGCTTACTGTT<br>TGTATTGCTGATGTGGCTTTCAGGCGAATATATGACTGCCAACGGTCAATGGGACTTAACGT<br>TCTGCAAACCGCCGACCACAAAATGCACCATACTTTTGTTGAAGCCGTGTGCCTGGGTATCCT<br>GGCAAACCTGATGGTCTGCCTTGCGGTATGGATGAGTTACTCCGGCCGTAGCCTGATGGATA<br>AAGCCATGATTATGGTTTTACCGGTGGCAATGTTTGTTGCCAGCGGGTTTGAGCACAGTATCG<br>CGAACATGTTTATGATCCCGCTGGGTATCGTTATCCGCGACTTTGCAAGCCCGGAATTCTGGA<br>CCGCAGTTGGTTCAACTCCGGAAAGTTTCTCTCACCTGACCGTCATGAACTTCATCACTGATA<br>ACCTGATTCCGGTAACTATCGGGAACATCATCGGCGGTGGTCTGCTGGTTGGGTTGACATAC<br>TGGGTCATTTACCTGCGTGGCGACGACCATCACTAAGGGTTGTTTCAGGCAGTAAATAAAAAA<br>TCCACTTAAGAAGGTAGGTGTTACATGTCCGAGCTTAATGAAAAGTTACAGCAGCAGGACGTT<br>ATTACTC |
| 11 | Ko_pflB_FP1 - ATCGGATCCGGGTCAACTGGCGAAAAACTGGCTCAACGT |
| 12 | Ko_pflB_RP1 - GAGTAATAACGTCCTGCTGCTGTAACTTTTCATTAAGCTCGGACAT |
| 13 | ATGTCCGAGCTTAATGAAAAGTTACAGCAGCAGGACGTTATTACTCGTACCTTCACTCAGACC<br>ATGTAATGGTATTGACTGAAATCGTACAGTAAAAAGCGTACAATAAAGGCTCCACGCAAGTGG<br>GGCCTTTTTAGCAATATCATCCTGCCCCAGTCTCTTTTGTCTGCTGTCTATACTTTATGGATAA<br>CAGCCAAAACAGACTCGACATAGCCTTTGAGCTGTGCATCTACATAGGCCCCGGATGGGCCA<br>AATTCGGAGATATCACCGCAATGTCAACAATTGGTCGCATTCACTCCTTTGAATCCTGTGGCA<br>CCGTCGATGGCCCGGGGATTCGCTTTATCACCTTCTTCCAGGGCTGCCTGATGCGCTGCCTC<br>TATTGCCACAACCGCGATACCTGGGATACCCACGGCGGCAAAGAGATTACCGTTGAAGAGCT<br>GATGAAAGAGGTGGTGACCTATCGCCACTTTATGAACGCTTCCGGCGGCGGCGTGACGGACA<br>TCCGGCGGCGAGGCTATCCTGCAGGCCGAATTTGTTCGCGACTGGTTCCGCGCCTGTAAGA<br>AAGAAGGTATTCATACCTGTCTCGATACCAACGGCTTTGTGCGCCGCTACGATCCGGTTATTG<br>ATGAACTGCTGGAGGTCACCGACCTGGTGATGCTCGATCTCAAGC |

TABLE 1-continued

| SEQ ID NO. | SEQUENCES |
|---|---|
| 14 | Ko_pflB_FP2 - ATGTCCGAGCTTAATGAAAAGTTACAGCAGCAGGACGTTATTACTC |
| 15 | Ko_pflB_RP2 - ACTGCGGCCGCGCTTGAGATCGAGCATCACCAGGTCGGTGA |
| 16 | GGGTCAACTGGCGAAAAACTGGCTCAACGTCTATGTTGGTAACCTGATTGGTTGCTTACTGTT<br>TGTATTGCTGATGTGGCTTTCAGGCGAATATATGACTGCCAACGGTCAATGGGGACTTAACGT<br>TCTGCAAACCGCCGACCACAAAATGCACCATACTTTTGTTGAAGCCGTGTGCCTGGGTATCCT<br>GGCAAACCTGATGGTCTGCCTTGCGGTATGGATGAGTTACTCCGGCCGTAGCCTGATGGATA<br>AAGCCATGATTATGGTTTTACCGGTGGCAATGTTTGTTGCCAGCGGGTTTGAGCACAGTATCG<br>CGAACATGTTTATGATCCCGCTGGGTATCGTTATCCGCGACTTTGCAAGCCCGGAATTCTGGA<br>CCGCAGTTGGTTCAACTCCGGAAAGTTTCTCTCACCTGACCGTCATGAACTTCATCACTGATA<br>ACCTGATTCCGGTAACTATCGGGAACATCATCGGCGGTGGTCTGCTGGTTGGGTTGACATAC<br>TGGGTCATTTACCTGCGTGGCGACGACCATCACTAAGGGTTGTTTCAGGCAGTAAATAAAAAA<br>TCCACTTAAGAAGGTAGGTGTTACATGTCCGAGCTTAATGAAAAGTTACAGCAGCAGGACGTT<br>ATTACTCGTACCTTCACTCAGACCATGTAATGGTATTGACTGAAATCGTACAGTAAAAAGCGTA<br>CAATAAAGGCTCCACGCAAGTGGGGCCTTTTTAGCAATATCATCCTGCCCCAGTCTCTTTTGT<br>CTGCTGTCTATACTTTATGGATAACAGCCAAAACAGACTCGACATAGCCTTTGAGCTGTGCAT<br>CTACATAGGCCCCGGATGGGCCAAATTCGGAGATATCACCGCAATGTCAACAATTGGTCGCA<br>TTCACTCCTTTGAATCCTGTGGCACCGTCGATGGCCCGGGGATTCGCTTTATCACCTTCTTCC<br>AGGGCTGCCTGATGCGCTGCCTCTATTGCCACAACCGCGATACCTGGGATACCCACGGCGG<br>CAAAGAGATTACCGTTGAAGAGCTGATGAAAGAGGTGGTGACCTATCGCCACTTTATGAACG<br>CTTCCGGCGGCGGCGTGACGGCATCCGGCGGCGAGGCTATCCTGCAGGCCGAATTTGTTC<br>GCGACTGGTTCCGCGCCTGTAAGAAAGAAGGTATTCATACCTGTCTCGATACCAACGGCTTTT<br>GTGCGCCGCTACGATCCGGTTATTGATGAACTGCTGGAGGTCACCGACCTGGTGATGCTCG<br>ATCTCAAGC |

Development of Recombinant Microorganism

The produced DNA fragments were transferred to *Klebsiella oxytoca* by using electroporation (25 uF, 200Ω, 18 kV/cm), and the target gene was capable of being removed by using a recombinant mechanism of the microorganism.

The DNA fragment including the homologous region of an ldha gene was transferred to a wild-type *Klebsiella oxytoca* to produce a recombinant *Klebsiella oxytoca* from which the ldha gene was removed (Comparative Example 2). Meanwhile, after the ldhA gene was removed from the wild-type *Klebsiella oxytoca*, the DNA fragment including the homologous region of a pflB gene was transferred to produce *Klebsiella oxytoca* from which the pflB gene was additionally removed together with the removal of the ldha gene (Example 1).

Electroporation was performed, and the recombinant microorganisms were cultured at 30° C. for 1 hour and stabilized. Then, the recombinant microorganisms were cultured by spreading them on an LB composite solid medium containing anti-biotics (such as kanamycin, chloramphenicol, and the like) at 37° C., respectively.

Figure 2:
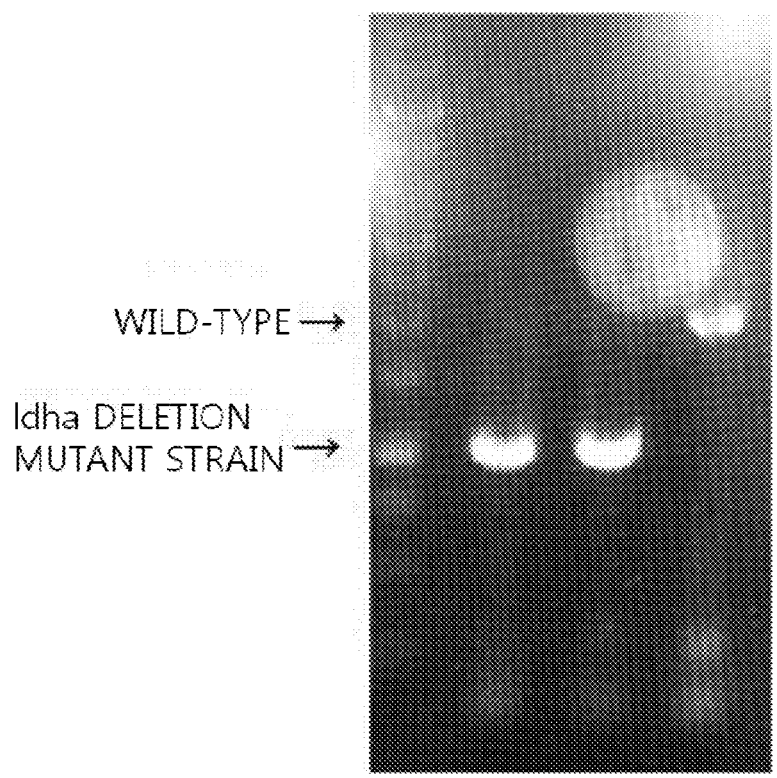
FIG. 2 is an agarose gel image obtained by PCR amplification and electrophoresis in order to confirm that ldhA which is a gene of lactate dehydrogenase associated with the occurrence of lactic acid is removed.
Figure 3:
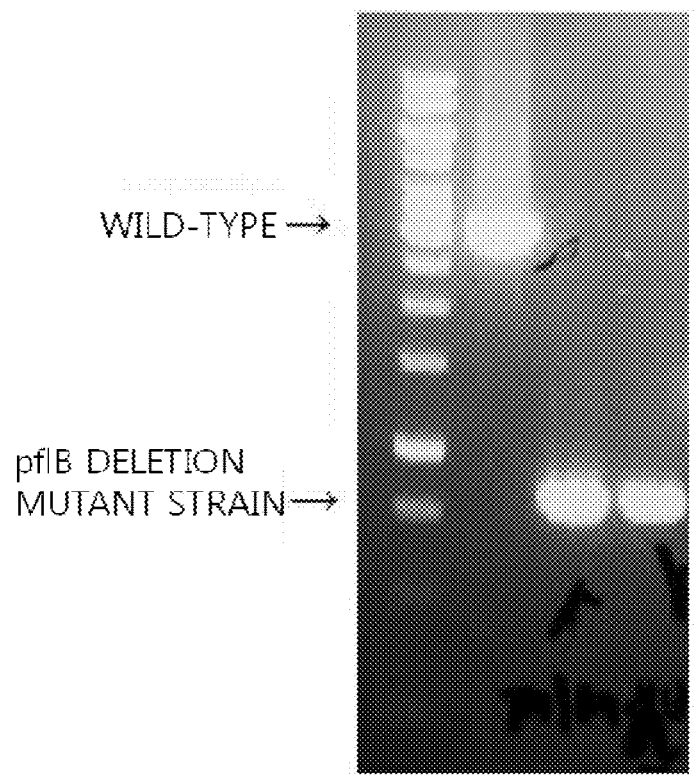
FIG. 3 is an agarose gel image obtained by PCR amplification and electrophoresis in order to confirm that pflB which is a gene of pyruvate-formate lyase associated with occurrence of formate is removed.

Then, colony PCR was performed on the colonies grown on the solid medium, and it was confirmed that the corresponding genes were removed from the colonies (FIG. 2 illustrates deletion of ldha and FIG. 3 illustrates deletion of pflB, respectively). Here, in order to confirm that the ldha gene was removed, PCR was performed with primers of SEQ ID NOs: 17 and 18, and in order to confirm that the pflB gene was removed, PCR was performed with primers of SEQ ID NOs: 19 and 20 (Table 2).

TABLE 2

| SEQ ID NO. | SEQUENCES |
|---|---|
| 17 | Ko_IdhA_Sc_FP - CCATCTGCATCGTATCCGCTGGCTTAAT |
| 18 | Ko_IdhA_Sc_RP - GCTGAAGCGGTTGCACATATTACCTG |
| 18 | Ko_pflB_Sc_FP - ACCATCACTAAGGGTTGTTTCAGGCAGTAA |
| 20 | Ko_pflB_Sc_RP - GCTAAAAAGGCCCCACTTGCGTGGAGCCTT |

In next test, a wild-type *Klebsiella oxytoca* was used as Comparative Example 1. Meanwhile, a recombinant *Klebsiella oxytoca* from which ldhA and adhE genes were deleted was produced by additionally deleting the adhE gene from the recombinant *Klebsiella oxytoca* from which ldha was deleted according to Comparative Example 2, the adhE gene being a gene encoding an alcohol dehydrogenation enzyme (aldehyde/alcohol dehydrogenase) directly involved in occurrence of ethanol. The produced recombinant *Klebsiella oxytoca* from which ldhA and adhE genes were deleted was tested as Comparative Example 3. The adhE gene was removed in a similar manner to the method for removing the ldhA gene or the pflB gene. The DNA fragment including the homologous region of the adhE gene was transferred to the *Klebsiella oxytoca* from which the ldha was removed, thereby producing *Klebsiella oxytoca* from which the adhE gene was additionally removed together with the removal of the ldha gene.

Experimental Example 2

Batch culture was performed by using microorganisms of Example 1, Comparative Examples 1 and 2 prepared in Experimental Example 1 above. First, *Klebsiella oxytoca* strains were inoculated in 250 ml of composite medium including 9 g/L glucose (50 mM) and cultured at 37° C. for 16 hours, and then the culture fluids were inoculated in 3 L of composite medium and cultured. Here, the fermentation was performed under a micro-aerobic condition (an aerobic speed of 1 vvm and an agitation speed of 150 rpm), at an initial glucose concentration of 90 g/L, pH 6.8, and a culture temperature of 37° C. 5N NH$_4$OH was used to control the pH during the fermentation. Samples for the *Klebsiella oxytoca* strains were taken during the fermentation, and growth rates were obtained by measuring optical density 600 (OD 600) of the taken samples. Then, the taken samples were centrifuged at 13,000 rpm for 10 minutes, and metabolites of supernatants and concentration of 2,3-butanediol thereof were analyzed by liquid chromatography (HPLC).

Figure 4:
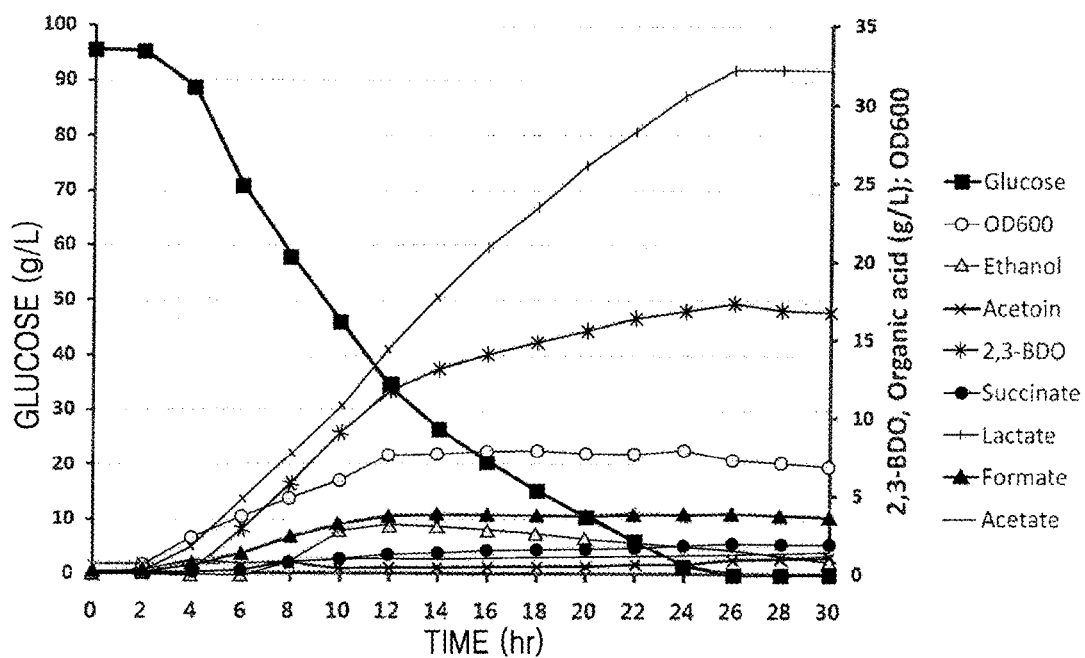
FIG. 4 illustrates fermentation results of a *Klebsiella oxytoca* strain of Comparative Example 1.
Figure 5:
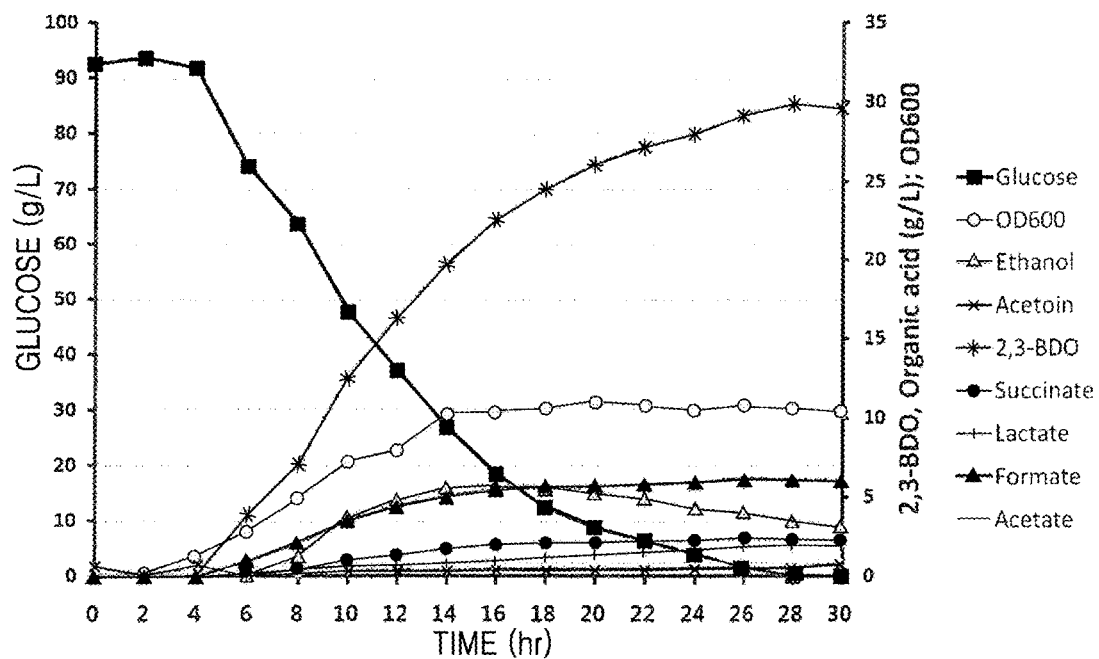
FIG. 5 illustrates fermentation results of a recombinant *Klebsiella oxytoca* strain of Comparative Example 2.

As a result, in the strain of Comparative Example 2, a production amount of 2,3-butanediol was 29.91 g/L, and a production yield of 2,3-butanediol (gram of 2,3-butanediol/gram of glucose) was 0.32. In addition, in the strain of Comparative Example 2, a productivity (g/L/h) of 2,3-butanediol was 1.07, and selectivity thereof was 59%. As compared to Comparative Example 1 which is a wild-type *Klebsiella oxytoca*, it was confirmed that the recombinant strain of Comparative Example 2 improved all of production concentration, production yield, productivity and selectivity of 2,3-butanediol while decreasing lactic acid production and increasing producing ability of 2,3-butanediol. However, the recombinant *Klebsiella oxytoca* of Comparative Example 2 still produced excessive amounts of by-products including formic acid and ethanol, which is considered as a cause of inhibiting a production concentration, a production yield, selectivity, and the like, of 2,3-butanediol of Comparative Example 2 (FIG. 4 illustrates Comparative Example 1 and FIG. 5 illustrates Comparative Example 2).

Meanwhile, as compared to Comparative Example 2 (*Klebsiella oxytoca* ΔldhA, 2,3-BDO 29.91 g/L), in the recombinant strain of Example 1, a production amount of 2,3-butanediol was increased to be 39.17±1.51 g/L. In addition, it was confirmed in the recombinant strain of Example 1 that a production amount of formic acid was decreased by 90% or more, and a production amount of ethanol was decreased by 73% or more, and a production yield of 2,3-butanediol (gram of 2,3-butanediol/gram of glucose) was also significantly increased from 0.32 to 0.45. Upon considering that a theoretical yield of 2,3-butanediol (a yield when it is assumed that all glucose supplied to *Klebsiella oxytoca* are converted to 2,3-butanediol) is 0.5, a yield of Example 1 (the theoretical yield thereof is 90%) was remarkably high.

Figure 6:
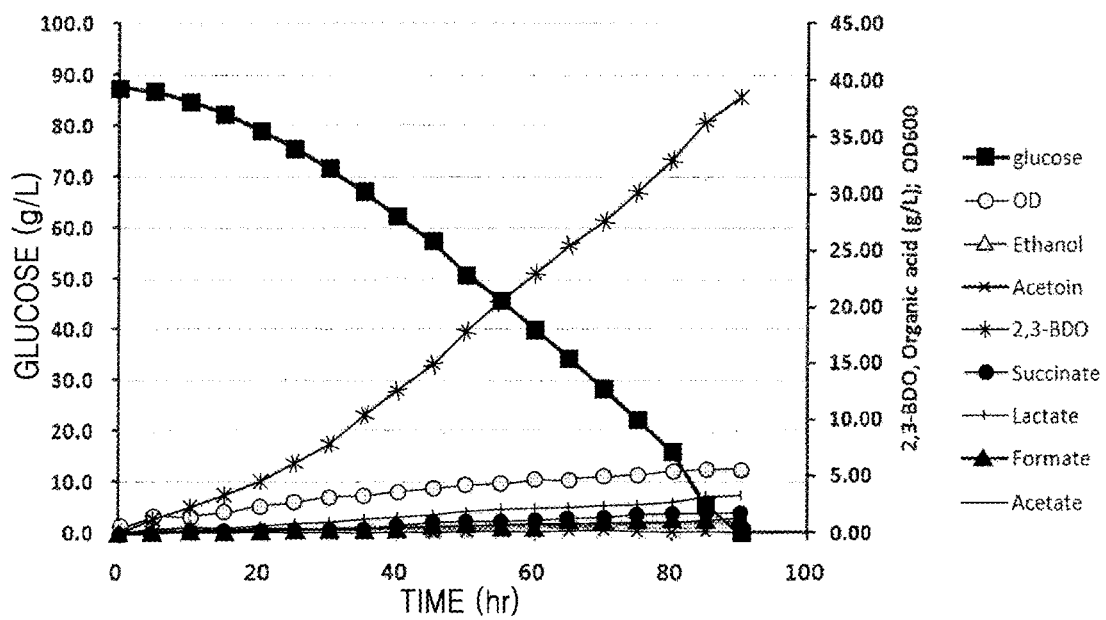
FIG. 6 illustrates fermentation results of a recombinant *Klebsiella oxytoca* strain of Example 1.
Figure 7:
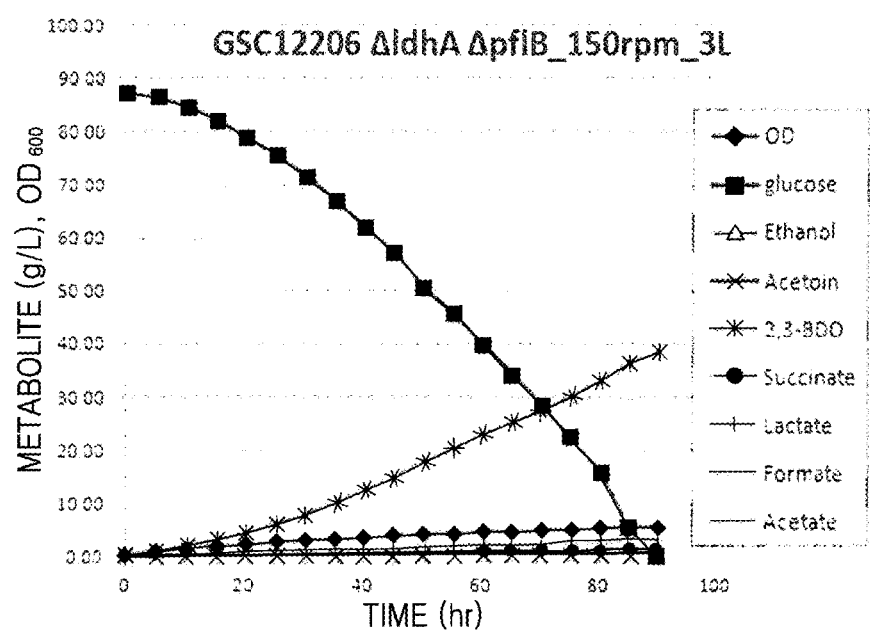
FIGS. 7 to 11 illustrate batch fermentation results of a recombinant *Klebsiella oxytoca* strain of Example 1 depending on an agitation speed of 150 rpm (FIG. 7), 250 rpm (FIG. 8), 350 rpm (FIG. 9), and 450 rpm (FIG. 10) (FIG. 11: concentrations of 2,3-butanediol per hour depending on agitation speed).
Figure 8:
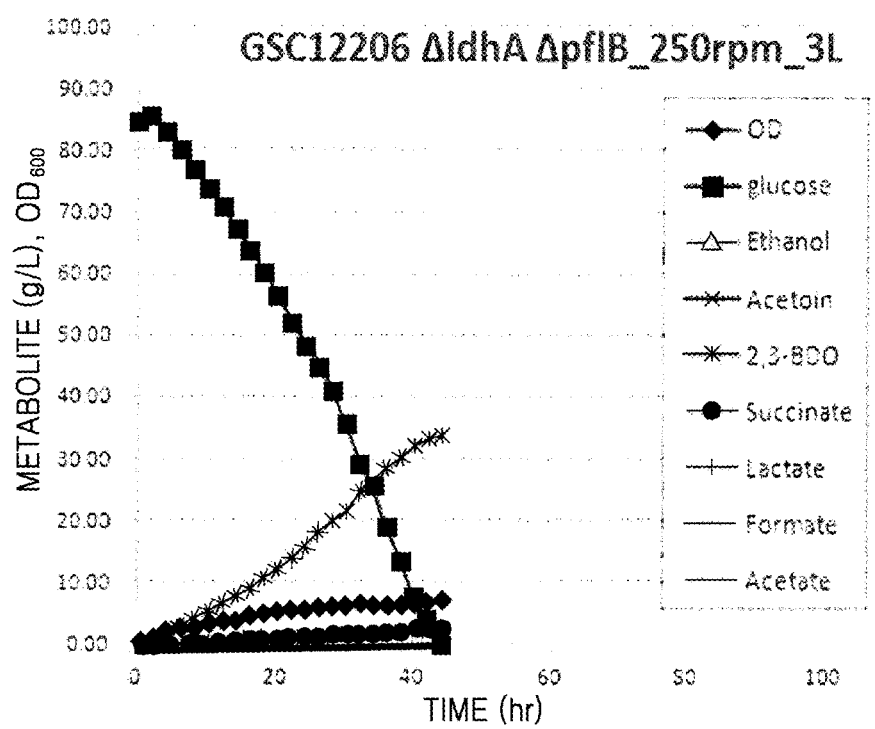
Figure 9:
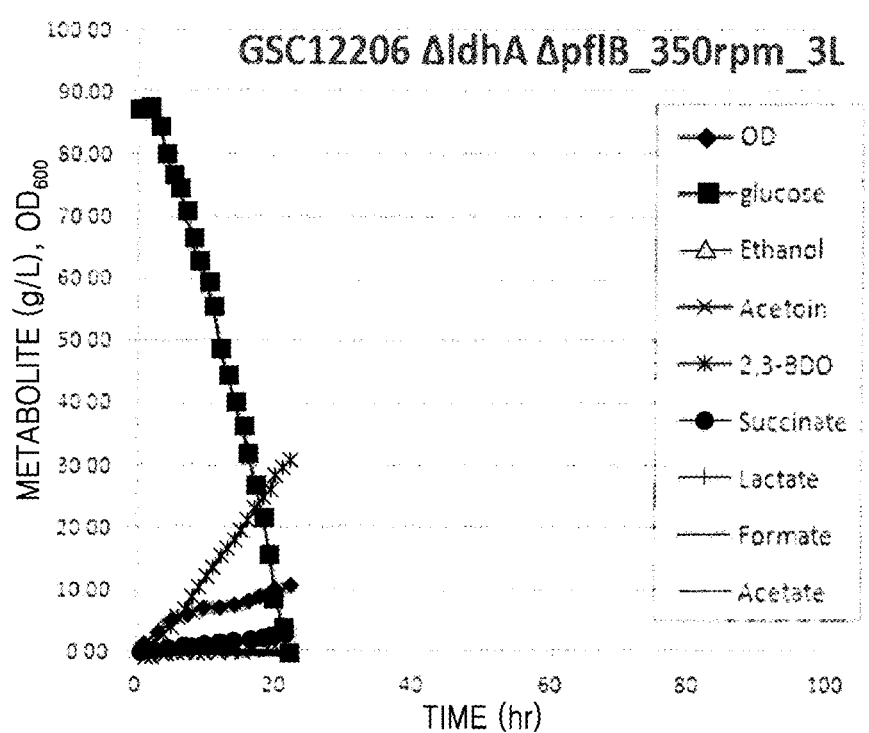
Figure 10:
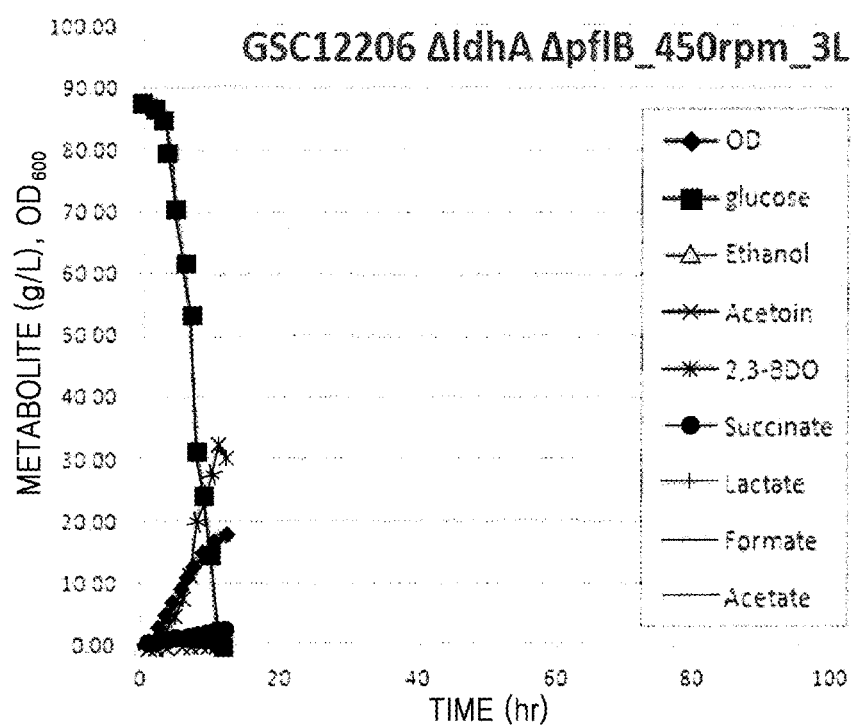
Figure 11:
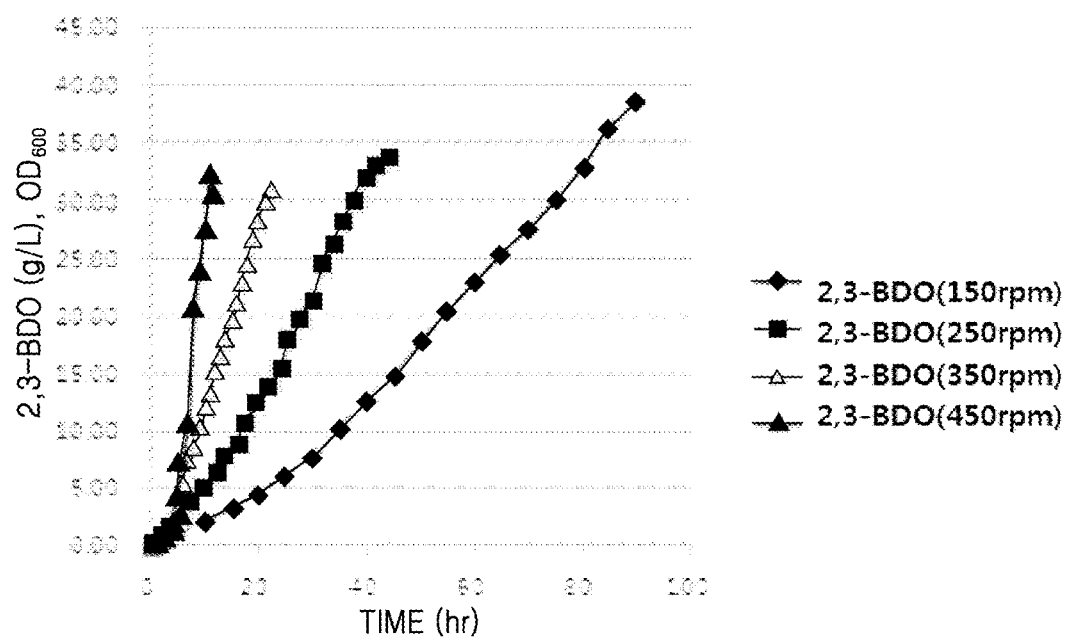

Accordingly, it could be confirmed that occurrence of by-products was remarkably decreased, and 2,3-butanediol was produced with high purity by simultaneously removing by-products such as formic acid, ethanol, and the like, through removal of the ldhA and the pflB genes. Regarding this, it could be continued that the removal of the gene (ldha) encoding the lactic acid dehydrogenation enzyme (lactate dehydrogenase) of *Klebsiella oxytoca* and the gene (pflB) encoding the pyruvate-formate lyase is significantly important for production of 2,3-butanediol in various stages of pathways for producing 2,3-butanediol (FIG. 6) (Table 3).

TABLE 3

| Strain | 2,3-butanediol | | | | Concentration (g/L) of by-products | | | | |
| --- | --- | --- | --- | --- | --- | --- | --- | --- | --- |
| | Concentration (g/L) | Yield (g/g) | Productivity (g/L/h) | Selectivity (%) | Lactate | Succinic Acid | Ethanol | Formic Acid | Acetic Acid |
| Comparative Example 1 | 17.31 | 0.18 | 0.58 | 27 | 32.20 | 1.92 | 1.61 | 3.88 | 1.27 |
| Comparative Example 2 | 29.91 | 0.32 | 1.07 | 59 | 1.93 | 2.27 | 3.54 | 6.11 | 0.92 |
| Example 1 | 39.17 ± 1.51 | 0.45 | 0.43 ± 0.02 | 83.33 ± 1.53 | 3.24 | 1.77 | 0.53 | 0.97 | 0.15 |

Experimental Example 3

Whether or not a producing ability of 2,3-butanediol was improved was tested at the time of removing a gene involved in occurrence of by-products in competition with biosynthesis of 2,3-butanediol in a 2,3-butanediol-producing microorganism. adhE is a gene encoding an alcohol dehydrogenation enzyme (aldehyde/alcohol dehydrogenase) directly involved in occurrence of ethanol which is a by-product in production of 2,3-butanediol. Accordingly, a recombinant *Klebsiella oxytoca* of Comparative Example 3 from which ldhA and adhE were removed was cultured and compared to that of Example 1. Here, culture conditions of the recombinant microorganism of Comparative Example 3 were the same as those of Experimental Example 2.

As a result, in Comparative Example 3 from which ldhA and adhE were simultaneously removed from *Klebsiella oxytoca*, a production amount of 2,3-butanediol was rather decreased to be 25.96 g/L as compared to Comparative Example 2 (*Klebsiella oxytoca* ΔldhA, 2,3-BDO 29.91 g/L). In addition, in Comparative Example 3, a production yield of 2,3-butanediol was 0.27, which was lower than that of Comparative Example 2 (0.32), and selectivity thereof was 55%, which was lower than that of Comparative Example 2 (59%), and productivity (g/L/h) was 0.36, which was remarkably lower than that of Comparative Example 2 (1.07). Further, in Comparative Example 3, a production amount of ethanol was decreased as compared to Comparative Example 2; however, a producing ability of 2,3-butanediol was rather deteriorated.

In addition, although being compared to Example 1, it could be appreciated that a producing ability of 2,3-butanediol of Comparative Example 3 was remarkably decreased (Table 4). Accordingly, it could be confirmed that even though the gene involved in occurrence of by-products was removed, it was not favorable to the production of 2,3-butanediol.

TABLE 4

| Strain | 2,3-butanediol | | | | Concentration (g/L) of by-products | | | | |
| --- | --- | --- | --- | --- | --- | --- | --- | --- | --- |
| | Concentration (g/L) | Yield (g/g) | Productivity (g/L/h) | Selectivity (%) | Lactate | Succinic Acid | Ethanol | Formic Acid | Acetic Acid |
| Comparative Example 1 | 17.31 | 0.18 | 0.58 | 27 | 32.20 | 1.92 | 1.61 | 3.88 | 1.27 |
| Comparative Example 2 | 29.91 | 0.32 | 1.07 | 59 | 1.93 | 2.27 | 3.54 | 6.11 | 0.92 |
| Comparative Example 3 | 25.96 | 0.27 | 0.36 | 55 | 2.71 | 2.32 | 0.89 | 4.13 | 6.43 |
| Example 1 | 39.17 ± 1.51 | 0.45 | 0.43 ± 0.02 | 83.33 ± 1.53 | 3.24 | 1.77 | 0.53 | 0.97 | 0.15 |

<Experimental Example 4> Change in Production of 2,3-Butanediol According to Change in Oxygen Supply Amount Effects of change in dissolved oxygen amount of a medium depending on an agitation speed during the culturing, on a production yield, a productivity, and selectivity of 2,3-butanediol were evaluated by using the recombinant Klebsiella oxytoca of Example 1.

First, the recombinant microorganism of Example 1 was inoculated in 250 ml of composite medium including 9 g/L glucose (50 mM) and cultured at 37° C. for 16 hours. Then, the obtained culture fluid was inoculated in 3 L of composite medium, and batch fermentation was performed. The fermentation was performed under a micro-aerobic condition (aerobic speed of 1 vvm), at an initial glucose concentration of 90 g/L, pH 6.8, and a culture temperature of 37° C., with a variety of agitation speeds, for example, 150 rpm, 250 rpm, 350 rpm, and 450 rpm. 5N $NH_4OH$ was used to control the pH during the fermentation. Samples for the recombinant Klebsiella oxytoca strains were taken during the fermentation, and growth rates were obtained by measuring optical density 600 (OD 600) of the taken samples. Then, the taken samples were centrifuged at 13,000 rpm for 10 minutes, and metabolites of supernatants and concentration of 2,3-butanediol (2,3-BDO) thereof were analyzed by liquid chromatography (HPLC).

As a result, in the recombinant Klebsiella oxytoca strain of Example 1, productivity (g/L/h) of 2,3-butanediol was largely changed depending on change in agitation speed. That is, it could be confirmed that at the time of agitating at an agitation speed of 450 rpm, productivity of 2,3-butanediol was increased by 5 times or more as compared to agitating at an agitation speed of 150 rpm (Table 5, FIGS. 7 to 11). It could be confirmed that the change in oxygen supply amount depending on the agitation speed could improve productivity of Example 1.

TABLE 5

| agitation Speed (rpm) | 2,3-Butanediol | | | |
| --- | --- | --- | --- | --- |
| | Concentration (g/L) | Yield (g/g) | Productivity (g/L/h) | Selectivity (%) |
| 150 | 39.17 ± 1.51 | 0.45 | 0.43 ± 0.02 | 83.33 ± 1.53 |
| 250 | 33.51 ± 0.23 | 0.39 ± 0.01 | 0.77 ± 0.02 | 84 |
| 350 | 31.39 ± 1.68 | 0.37 ± 0.02 | 1.40 ± 0.12 | 80 ± 1.00 |
| 450 | 30.79 ± 1.46 | 0.35 ± 0.02 | 2.71 ± 0.21 | 84 ± 4.58 |

<Experimental Example 5> Production of 2,3-Butanediol Through Fed-Batch Fermentation Under Aerobic Condition (Agitating at Agitation Speed of 450 Rpm)

Fed-batch fermentation for production of 2,3-butanediol was performed by using the strain of Example 1 while maintaining an agitation speed at 450 rpm which exhibited the most improved productivity based on the results of Experimental Example 4.

First, the recombinant Klebsiella oxytoca strain of Example 1 was inoculated in 250 ml of composite medium including 9 g/L glucose (50 mM) and cultured at 37° C. for 16 hours, and then the obtained culture fluid was inoculated in 3 L of composite medium and fed-batch culture was performed. Here, the fermentation was performed under a micro-aerobic condition (aerobic speed of 1 vvm), at an initial glucose concentration of 90 g/L, pH 6.8, and a culture temperature of 37° C. The agitation speed was continuously maintained at 450 rpm. 5N $NH_4OH$ was used to control the pH during the fermentation. When a glucose concentration was decreased to be 10 g/L or less during the fermentation, a glucose solution of 700 g/L or more was fed. A sample for the recombinant Klebsiella oxytoca strain was taken during the fermentation, and a growth rate was obtained by measuring optical density 600 (OD 600) of the taken sample. Then, the taken sample was centrifuged at 13,000 rpm for 10 minutes, and a metabolite of supernatant and concentration of 2,3-butanediol thereof were analyzed by liquid chromatography (HPLC).

Figure 12:
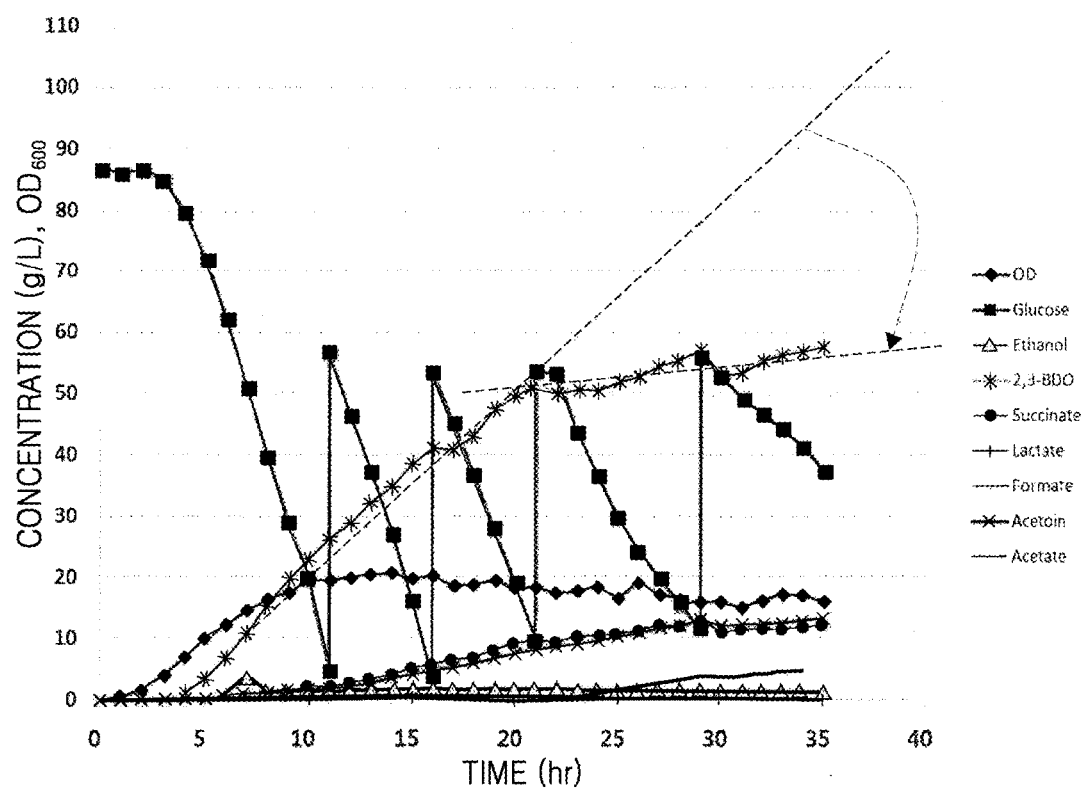
FIG. 12 illustrates fed-batch fermentation results of a recombinant *Klebsiella oxytoca* strain of Example 1 performed by retaining an agitation speed at 450 rpm under aerobic condition.

As a result, it could be confirmed that when the agitation speed was continuously maintained at 450 rpm, a producing ability of 2,3-butanediol was not continuously maintained (Table 6). In particular, it could be confirmed that when a concentration of acetoin was over 10 g/L, the producing ability of 2,3-butanediol was remarkably decreased (FIG. 12). It could be appreciated that the agitation speed of the fed-batch culture was required to be controlled based on results of the fed-batch culture performed at the agitation speed maintained at 450 rpm, and a time point for controlling the agitation speed was required to be determined based on the concentration of acetoin to be accumulated.

TABLE 6

| | 2,3-Butanediol | | | | | | |
| Strain | Concentration (g/L) | Productivity (g/L/h) | Yield (g/g) | Selectivity (%) | Acetoin (g/L) | Succinic Acid (g/L) | Acetic Acid (g/L) |
| --- | --- | --- | --- | --- | --- | --- | --- |
| Example 1 | 57.7 | 1.65 | 29 | 63 | 13.44 | 12.38 | 5.32 |

<Experimental Example 6> Production of 2,3-Butanediol Through Fed-Batch Fermentation The recombinant *Klebsiella oxytoca* strain of Example 1 was inoculated in 250 ml of composite medium including 9 g/L glucose (50 mM) and cultured at 37° C. for 16 hours. Then, the obtained culture fluid was inoculated in 3 L of composite medium, and fed-batch culture was performed. Here, the fermentation was performed under a micro-aerobic condition (aerobic speed of 1 vvm), at an initial glucose concentration of 90 g/L, pH 6.8, a culture temperature of 37° C., and an agitation speed of 450 rpm. 5N $NH_4OH$ was used to control the pH during the fermentation. When a glucose concentration was decreased to be 10 g/L or less during the fermentation, a glucose solution of 700 g/L or more was fed. In addition, at a time point at which the concentration of acetoin which is one of the by-products, is 7 g/L, the fermentation was performed by changing the agitation speed from 450 rpm to 350 rpm. A sample for the recombinant *Klebsiella oxytoca* strain was taken during the fermentation, and a growth rate was obtained by measuring optical density 600 (OD 600) of the taken sample. Then, the taken sample was centrifuged at 13,000 rpm for 10 minutes, and a metabolite of supernatant and concentration of 2,3-butanediol thereof were analyzed by liquid chromatography (HPLC).

Figure 13:
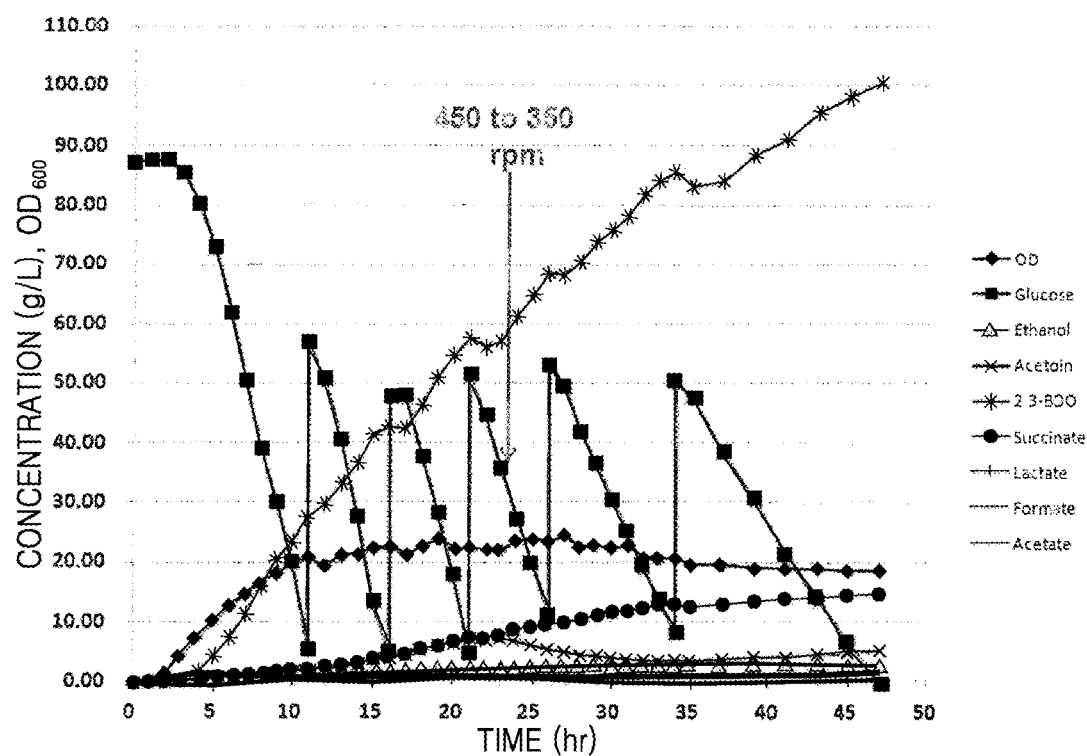
FIG. 13 illustrates fed-batch fermentation results of a recombinant *Klebsiella oxytoca* strain of Example 1 performed by controlling an agitation speed.

As a result, as compared to the fed-batch culture performed by uniformly maintaining the agitation speed at 450 rpm in Experimental Example 5, all of the concentration, the productivity, the yield, and the selectivity of 2,3-butanediol were largely increased by 74.5%, 29.7%, 55.2%, and 27.0%, respectively. Therefore, it could be confirmed that the production of 2,3-butanediol using the recombinant strain of Example 1 was largely affected by the control of the dissolved oxygen amount depending on the agitation speed. Accordingly, it was determined that the productivity of 2,3-butanediol could be improved by controlling the agitation speed to control the dissolved oxygen amount in the medium (Table 7, FIG. 13).

TABLE 7

| | 2,3-Butanediol | | | | | |
| Strain | Concentration (g/L) | Productivity (g/L/h) | Selectivity (%) | Acetoin (g/L) | Succinic Acid (g/L) | Acetic Acid (g/L) |
| --- | --- | --- | --- | --- | --- | --- |
| Example 1 | 100.66 | 2.14 | 80 | 5.19 | 14.76 | 2.73 |

INDUSTRIAL APPLICABILITY

The present invention relates to a recombinant microorganism having enhanced 2,3-butanediol producing ability, wherein a pathway for converting pyruvate to acetyl-CoA, a pathway for converting pyruvate to formic acid, or a pathway for converting pyruvate to lactate is inhibited in a microorganism having acetyl-CoA and lactate biosynthetic pathways. The recombinant microorganism of the present invention may produce 2,3-butanediol with high selectivity and concentration.

The invention claimed is:

1. A recombinant microorganism having enhanced 2,3-butanediol producing ability and decreased lactate producing ability, decreased ethanol producing ability, decreased formic acid producing ability and decreased acetic acid producing ability as compared to a corresponding wild-type microorganism,
   wherein an ldhA gene encoding a lactate dehydrogenase and a pflB gene encoding a pyruvate formate lyase are deleted in the recombinant microorganism,
   wherein the recombinant microorganism is a recombinant *Klebsiella oxytoca* microorganism, and the corresponding wild-type microorganism is a wild-type *Klebsiella oxytoca* microorganism,
   wherein the recombinant microorganism has higher selectivity of 2,3-butanediol or higher 2,3-butanediol productivity than a recombinant *Klebsiella oxytoca* in which an ldhA gene and a gene encoding alcohol dehydrogenation enzyme which converts acetyl-CoA to ethanol are deleted,
   wherein the recombinant microorganism has a selectivity of 2,3-butanediol of 70% or more based on batch culture or fed-batch culture, wherein the selectivity of 2,3-butanediol is calculated as:

selectivity of 2,3-butanediol (%)={Production amount (g) of 2,3-butanediol/(production amounts (g) of 2,3-butanediol,ethanol,acetoin, succinic acid,lactate,formate, and acetic acid)}× 100, and wherein the 2,3-butanediol productivity is calculated as:
   2,3-butanediol productivity (g/L/h): an amount of 2,3-butanediol in grams produced per unit time of hours and unit volume of liters.

2. The recombinant microorganism of claim 1, wherein a yield of 2,3-butanediol is 0.35 gram or more per gram of carbon source.

3. A method for producing 2,3-butanediol, the method comprising:
   culturing the recombinant microorganism of claim 1 in a cell culture under conditions suitable for the production of 2,3-butanediol; and
   recovering 2,3-butanediol from the culture.

4. The method of claim 3, wherein the culturing is performed under aerobic conditions.

5. The method of claim 3, wherein the culturing comprises agitating the culture at an agitation speed of 450 rpm or less.

6. The method of claim 3, wherein the culturing comprises agitating the culture, and reducing agitation speed when a concentration of acetoin in the culture is 5 g/L or more.

7. The method of claim 3, wherein the culturing comprises controlling an amount of oxygen supply to the culture to control 2,3-butanediol productivity.

8. The method of claim 3, wherein the culturing comprises agitating the culture, and controlling agitation speed to control 2,3-butanediol productivity.

* * * * *

SEQUENCE LISTING

<160> NUMBER OF SEQ ID NOS: 20

<210> SEQ ID NO 1
<211> LENGTH: 990
<212> TYPE: DNA
<213> ORGANISM: Klebsiella oxytoca

<400> SEQUENCE: 1

```
atgaaaatcg ctgtgtatag tacaaaacag tacgacaaga agtatctgca gcatgttaat      60
gatgcatatg gctttgaact ggagtttttt gacttcctgc taaccgaaaa aaccgccaaa     120
accgccaacg gctgtgaagc ggtgtgtatc ttcgtaaacg atgacggtag ccgcccggta     180
cttgaagaac tgaaagccca cggcgtgcag tacatcgcgc tgcgctgcgc ggggttcaac     240
aacgttgacc tcgatgccgc caaagagctg ggcctgcggg tggtgcgcgt cccggcctac     300
tcgccggaag cggtcgctga gcacgcgatc ggcatgatga tgtcgctgaa ccgccgcatt     360
caccgtgcct atcagcgcac ccgcgacgcg aacttctctc tggaagggct gaccggtttc     420
accatgcacg gtaaaaccgc cggcgttatt ggcaccggta aaatcggcgt cgccgcgctg     480
cgcattctta aaggcttcgg tatgcgtctg ctggcgtttg atccctaccc aagcgccgcc     540
```

```
gcgctggata tgggcgtgga gtatgtcgat cttgaaaccc tgtaccggga gtccgatgtt    600
atctcactgc actgcccact gaccgatgaa aactaccatt tgctgaacca tgccgcgttc    660
gatcgcatga aagacggggt gatgatcatc aacaccagcc gcggcgcgct catcgattcg    720
caggcagcga tcgacgccct gaagcatcag aaaattggcg cgctggggat ggacgtgtat    780
gagaacgaac gcgatctgtt cttttgaagat aagtctaatg acgtgattca ggatgatgtg    840
ttccgccgtc tctccgcctg ccataacgtc ctgtttaccg gtcaccaggc gtttctgacc    900
gcggaagcgt tgatcagcat ttcgcaaacc accctcgaca acctgcgtca agtggatgca    960
ggcgaaacct gtcctaacgc actggtctga                                     990
```

```
<210> SEQ ID NO 2
<211> LENGTH: 595
<212> TYPE: DNA
<213> ORGANISM: Artificial
<220> FEATURE:
<223> OTHER INFORMATION: homologue of ldhA gene

<400> SEQUENCE: 2
atgacgttcg ctaaatcctg cgccgtcatc tcgctgctga tcccgggcac ctccgggcta    60
ctgctgttcg gcaccctggc atcggccagc ccgggacatt tcctgttaat gtggatgagc    120
gccagcctcg gcgctatcgg cggattctgg ctctcgtggc tgacgggcta ccgctaccgg    180
taccatctgc atcgtatccg ctggcttaat gccgaacgcc tcgctcgcgg ccagttgttc    240
ctgcgccgcc acggcgcgtg ggcagtcttt tttagccgct ttctctctcc gcttcgcgcc    300
accgtgccgc tggtaaccgg cgccagcggc acctctctct ggcagtttca gctcgccaac    360
gtcagctccg gctgctctg gccgctgatc ctgctggcgc caggcgcgtt aagcctcagc    420
ttttgatgaa aggtattgtc tttttaaagag atttcttaac accgcgatat gctctagaat    480
tattactata acctgctgat taaactagtt tttaacattt gtaagattat tttaattatg    540
ctaccgtgac ggtattatca ctggagaaaa gtcttttttc cttgcccttt tgtgc         595
```

```
<210> SEQ ID NO 3
<211> LENGTH: 30
<212> TYPE: DNA
<213> ORGANISM: Artificial
<220> FEATURE:
<223> OTHER INFORMATION: primer

<400> SEQUENCE: 3
cacggatcca tgacgttcgc taaatcctgc                                     30
```

```
<210> SEQ ID NO 4
<211> LENGTH: 40
<212> TYPE: DNA
<213> ORGANISM: Artificial
<220> FEATURE:
<223> OTHER INFORMATION: primer

<400> SEQUENCE: 4
gcacaaaagg gcaaggaaaa aagactttc tccagtgata                           40
```

```
<210> SEQ ID NO 5
<211> LENGTH: 591
<212> TYPE: DNA
<213> ORGANISM: Artificial
<220> FEATURE:
<223> OTHER INFORMATION: homologue of ldhA gene

<400> SEQUENCE: 5
```

```
tatcactgga gaaaagtctt ttttccttgc cctttttgtgc tcccccttcg cggggggcac    60
attcagataa tccccacaga aattgcctgc gataaagtta caatcccttc atttattaat   120 acgataaaata tttatggaga ttaaatgaac aagtatgctg cgctgctggc ggtgggaatg   180
ttgctatcgg gctgcgttta acagcaag gtgtcgacca gagcggaaca gcttcagcac    240
caccgttttg tgctgaccag cgttaacggg cagccgctga atgccgcgga taagccgcag   300
gagctgagct tcggcgaaaa gatgcccatt acgggcaaga tgtctgtttc aggtaatatg   360
tgcaaccgct tcagcggcac gggcaaagtc tctgacggcg agctgaaggt tgaagagctg   420
gcaatgaccc gcatgctctg cacggactcg cagcttaacg ccctggacgc cacgctgagc   480
aaaatgctgc gcgaaggcgc gcaggtcgac ctgacggaaa cgcagctaac gctggcgacc   540
gccgaccaga cgctggtgta taagctcgcc gacctgatga attaataatt a            591

<210> SEQ ID NO 6
<211> LENGTH: 40
<212> TYPE: DNA
<213> ORGANISM: Artificial
<220> FEATURE:
<223> OTHER INFORMATION: primer

<400> SEQUENCE: 6
tatcactgga gaaaagtctt ttttccttgc cctttttgtgc                         40

<210> SEQ ID NO 7
<211> LENGTH: 32
<212> TYPE: DNA
<213> ORGANISM: Artificial
<220> FEATURE:
<223> OTHER INFORMATION: primer

<400> SEQUENCE: 7
cctgcggccg ctaattatta attcatcagg tc                                   32

<210> SEQ ID NO 8
<211> LENGTH: 1146
<212> TYPE: DNA
<213> ORGANISM: Artificial
<220> FEATURE:
<223> OTHER INFORMATION: dna fragment

<400> SEQUENCE: 8
atgacgttcg ctaaatcctg cgccgtcatc tcgctgctga tcccgggcac ctccgggcta    60
ctgctgttcg gcaccctggc atcggccagc ccgggacatt tcctgttaat gtggatgagc   120
gccagcctcg gcgctatcgg cggattctgg ctctcgtggc tgacgggcta ccgctaccgg   180
taccatctgc atcgtatccg ctggcttaat gccgaacgcc tcgctcgcgg ccagttgttc   240
ctgcgccgcc acggcgcgtg ggcagtcttt tttagccgct ttctctctcc gcttcgcgcc   300
accgtgccgc tggtaaccgg cgccagcggc acctctctct ggcagtttca gctcgccaac   360
gtcagctccg ggctgctctg gccgctgatc ctgctggcgc aggcgcgtt aagcctcagc   420 ttttgatgaa aggtattgtc ttttaaagag atttcttaac accgcgatat gctctagaat   480
tattactata acctgctgat taaactagtt tttaacattt gtaagattat tttaattatg   540
ctaccgtgac ggtattatca ctggagaaaa gtctttttttc cttgcccttt tgtgctcccc   600
cttcgcgggg ggcacattca gataatcccc acagaaattg cctgcgataa agttacaatc   660
ccttcattta ttaatacgat aaaatatttat ggagattaaa tgaacaagta tgctgcgctg   720
```

```
ctggcggtgg gaatgttgct atcgggctgc gtttataaca gcaaggtgtc gaccagagcg      780
gaacagcttc agcaccaccg tttttgtgctg accagcgtta acgggcagcc gctgaatgcc      840
gcggataagc cgcaggagct gagcttcggc gaaaagatgc ccattacggg caagatgtct      900
gtttcaggta atatgtgcaa ccgcttcagc ggcacgggca agtctctga cggcgagctg      960 aaggttgaag agctggcaat gacccgcatg ctctgcacgg actcgcagct taacgccctg     1020
gacgccacgc tgagcaaaat gctgcgcgaa ggcgcgcagg tcgacctgac ggaaacgcag     1080
ctaacgctgg cgaccgccga ccagacgctg gtgtataagc tcgccgacct gatgaattaa     1140
taatta                                                                1146

<210> SEQ ID NO 9
<211> LENGTH: 2283
<212> TYPE: DNA
<213> ORGANISM: Klebsiella oxytoca

<400> SEQUENCE: 9
atgtccgagc ttaatgaaaa gttagccaca gcctgggaag gttttgcgaa aggtgactgg       60
cagaacgaag tcaacgtccg cgacttcatc cagaaaaact ataccccgta cgaaggtgac      120
gagtccttcc tggctggcgc aactgacgcg accaccaagc tgtgggacac cgtaatggaa      180
ggcgttaaac aggaaaaccg cactcacgcg cctgttgatt ttgatacttc ccttgcatcc      240
accatcactt tcatgacgc tggctacatc gagaaaggtc tcgagaaaat cgttggtctg      300
cagactgaag ctccgctgaa acgcgcgatt atcccgttcg gcggcatcaa aatggtcgaa      360
ggttcctgca agcgtacga tcgcgagctg gacccgatgc tgaagaaaat cttcactgaa      420
taccgtaaaa ctcacaacca gggcgtgttt gacgtttaca ccaaagacat cctgaactgc      480
cgtaaatctg tgttctgac cggtctgccg atgcctatg gccgtggtcg tatcatcggt      540
gactaccgtc gcgttgcgct gtacggtatc gacttcctga tgaaagacaa atacgctcag      600
ttcgtttctc tgcaagagaa actggaaaac ggcgaagatc tggaagcaac catccgtctg      660
cgcgaagaaa tctctgaaca gcaccgcgcg ctgggtcaga tcaaagaaat ggcggctaaa      720
tatgcctgcg atatctctgg tcctgctacc accgctcagg aagctatcca gtggacctac      780
ttcggttacc tggctgccgt aaaatctcag aacggcgcgg caatgtcctt cggtcgtacc      840
tccagcttcc tggacatctt catcgaacgt gacctgaaag ccggtaaaat caccgagcaa      900
gacgcacagg aaatgattga ccacctggtc atgaaactgc gtatggttcg tttcctgcgt      960 accccctgaat atgatgaact gttctctggc gacccgatct gggcaacaga atctatcggc     1020
ggtatgggcg ttgacggccg tactctggtc accaaaaaca gcttccgttt cctgaacacc     1080
ctgtacacca tggggccgtc tccggagccg aacatcacca ttctgtggtc tgaaaaactg     1140
ccgctgagct tcaaaaaata cgccgcgaaa gtgtccatcg atacctcttc tctgcagtac     1200
gagaacgatg acctgatgcg tcctgacttc aacaacgatg actacgctat cgcttgctgc     1260
gtaagcccga tggttgttgg taagcaaatg cagttcttcg gcgcgcgtgc taacctggcg     1320
aaaaccatgc tgtacgcaat caacggcggc gttgatgaaa aactgaaaat gcaggttggt     1380
cctaaatctg aaccgatcaa aggcgacgtt ctgaacttcg acgaagtgat ggaccgcatg     1440
gatcacttca tggactggct ggctaaacag tacgtcactg cgctgaacat catccactac     1500
atgcacgaca gtacagcta cgaagcttcc ctgatggcgc tgcacgaccg tgatgttatc     1560
cgcaccatgg catgtggtat cgcaggtctt tccgttgcgg ctgactccct gtctgcaatc     1620
aaatatgcga agttaaacc gattcgtgac gaaaacggtc tggctgtcga cttcgaaatc     1680
```

```
gaaggcgaat acccgcagtt tggtaacaac gactctcgcg tcgatgatat ggccgttgac    1740
ctggttgaac gtttcatgaa gaaaattcag aaactgcaca cctaccgcaa cgctatcccg    1800
actcagtccg ttctgaccat cacctctaac gttgtgtatg gtaagaaaac cggcaacacc    1860
cctgacggtc gtcgcgctgg cgctccgttc ggaccaggtg ctaacccgat gcacggccgt    1920
gaccagaaag gcgctgttgc ctctctgacc tccgttgcaa aactgccgtt tgcttacgcg    1980
aaagatggta tttcttacac cttctctatc gtgccgaacg cgctgggtaa agacgacgaa    2040
gttcgtaaaa ctaacctcgc cggcctgatg gatggttact tccaccacga agcgtccatc    2100
gaaggcggtc agcatctgaa cgtcaacgtt atgaaccgcg aaatgctgct cgacgcgatg    2160
gaaaacccgg aaaaatatcc gcagctgacc atccgcgtat ccggctacgc agtacgtttt    2220
aactccctga ctaaagaaca gcagcaggac gttattactc gtaccttcac tcagaccatg    2280
taa                                                                  2283

<210> SEQ ID NO 10
<211> LENGTH: 635
<212> TYPE: DNA
<213> ORGANISM: Artificial
<220> FEATURE:
<223> OTHER INFORMATION: homologue of pflB gene

<400> SEQUENCE: 10
gggtcaactg gcgaaaaact ggctcaacgt ctatgttggt aacctgattg gttgcttact      60
gtttgtattg ctgatgtggc tttcaggcga atatatgact gccaacggtc aatggggact     120
taacgttctg caaaccgccg accacaaaat gcaccatact tttgttgaag ccgtgtgcct     180
gggtatcctg gcaaacctga tggtctgcct tgcggtatgg atgagttact ccggccgtag     240
cctgatggat aaagccatga ttatggtttt accggtggca atgtttgttg ccagcgggtt     300
tgagcacagt atcgcgaaca tgtttatgat cccgctgggt atcgttatcc gcgactttgc     360
aagcccggaa ttctggaccg cagttggttc aactccggaa agtttctctc acctgaccgt     420
catgaacttc atcactgata acctgattcc ggtaactatc gggaacatca tcggcggtgg     480
tctgctggtt gggttgacat actgggtcat ttacctgcgt ggcgacgacc atcactaagg     540
gttgtttcag gcagtaaata aaaaatccac ttaagaaggt aggtgttaca tgtccgagct     600
taatgaaaag ttacagcagc aggacgttat tactc                                635

<210> SEQ ID NO 11
<211> LENGTH: 39
<212> TYPE: DNA
<213> ORGANISM: Artificial
<220> FEATURE:
<223> OTHER INFORMATION: primer

<400> SEQUENCE: 11
atcggatccg ggtcaactgg cgaaaaactg gctcaacgt                             39

<210> SEQ ID NO 12
<211> LENGTH: 46
<212> TYPE: DNA
<213> ORGANISM: Artificial
<220> FEATURE:
<223> OTHER INFORMATION: primer

<400> SEQUENCE: 12
gagtaataac gtcctgctgc tgtaactttt cattaagctc ggacat                     46
```

<210> SEQ ID NO 13
<211> LENGTH: 669
<212> TYPE: DNA
<213> ORGANISM: Artificial
<220> FEATURE:
<223> OTHER INFORMATION: homologue of pflB gene

<400> SEQUENCE: 13

| | | | | | |
|---|---|---|---|---|---|
| atgtccgagc | ttaatgaaaa | gttacagcag | caggacgtta | ttactcgtac | cttcactcag | 60 |
| accatgtaat | ggtattgact | gaaatcgtac | agtaaaaagc | gtacaataaa | ggctccacgc | 120 |
| aagtggggcc | ttttagcaa | tatcatcctg | ccccagtctc | ttttgtctgc | tgtctatact | 180 |
| ttatggataa | cagccaaaac | agactcgaca | tagcctttga | gctgtgcatc | tacataggcc | 240 |
| ccggatgggc | caaattcgga | gatatcaccg | caatgtcaac | aattggtcgc | attcactcct | 300 |
| ttgaatcctg | tggcaccgtc | gatggcccgg | ggattcgctt | tatcaccttc | ttccagggct | 360 |
| gcctgatgcg | ctgcctctat | tgccacaacc | gcgatacctg | gataccccac | ggcggcaaag | 420 |
| agattaccgt | tgaagagctg | atgaaagagg | tggtgaccta | tcgccacttt | atgaacgctt | 480 |
| ccggcggcgg | cgtgacggca | tccggcggcg | aggctatcct | gcaggccgaa | tttgttcgcg | 540 |
| actggttccg | cgcctgtaag | aaagaaggta | ttcatacctc | tctcgatacc | aacggctttg | 600 |
| tgcgccgcta | cgatccggtt | attgatgaac | tgctggaggt | caccgacctg | gtgatgctcg | 660 |
| atctcaagc | | | | | | 669 |

<210> SEQ ID NO 14
<211> LENGTH: 46
<212> TYPE: DNA
<213> ORGANISM: Artificial
<220> FEATURE:
<223> OTHER INFORMATION: primer

<400> SEQUENCE: 14
atgtccgagc ttaatgaaaa gttacagcag caggacgtta ttactc    46

<210> SEQ ID NO 15
<211> LENGTH: 41
<212> TYPE: DNA
<213> ORGANISM: Artificial
<220> FEATURE:
<223> OTHER INFORMATION: primer

<400> SEQUENCE: 15
actgcggccg cgcttgagat cgagcatcac caggtcggtg a    41

<210> SEQ ID NO 16
<211> LENGTH: 1258
<212> TYPE: DNA
<213> ORGANISM: Artificial
<220> FEATURE:
<223> OTHER INFORMATION: dna fragment

<400> SEQUENCE: 16

| | | | | | |
|---|---|---|---|---|---|
| gggtcaactg | gcgaaaaact | ggctcaacgt | ctatgttggt | aacctgattg | gttgcttact | 60 |
| gtttgtattg | ctgatgtggc | tttcaggcga | atatatgact | gccaacggtc | aatgggact | 120 |
| taacgttctg | caaaccgccg | accacaaaat | gcaccatact | tttgttgaag | ccgtgtgcct | 180 |
| gggtatcctg | gcaaacctga | tggtctgcct | tgcggtatgg | atgagttact | ccggccgtag | 240 |
| cctgatggat | aaagccatga | ttatggtttt | accggtggca | atgtttgttg | ccagcggggtt | 300 |
| tgagcacagt | atcgcgaaca | tgtttatgat | cccgctgggt | atcgttatcc | gcgactttgc | 360 |

-continued

```
aagcccggaa ttctggaccg cagttggttc aactccggaa agtttctctc acctgaccgt     420
catgaacttc atcactgata acctgattcc ggtaactatc gggaacatca tcggcggtgg     480
tctgctggtt gggttgacat actgggtcat ttacctgcgt ggcgacgacc atcactaagg     540
gttgtttcag gcagtaaata aaaaatccac ttaagaaggt aggtgttaca tgtccgagct     600
taatgaaaag ttacagcagc aggacgttat tactcgtacc ttcactcaga ccatgtaatg     660
gtattgactg aaatcgtaca gtaaaaagcg tacaataaag gctccacgca agtggggcct     720
ttttagcaat atcatcctgc cccagtctct tttgtctgct gtctatactt tatggataac     780
agccaaaaca gactcgacat agcctttgag ctgtgcatct acataggccc cggatgggcc     840
aaattcggag atatcaccgc aatgtcaaca attggtcgca ttcactcctt tgaatcctgt     900
ggcaccgtcg atggcccggg gattcgcttt atcaccttct tccagggctg cctgatgcgc     960
tgcctctatt gccacaaccg cgatacctgg gataccacg gcggcaaaga gattaccgtt    1020
gaagagctga tgaaagaggt ggtgacctat cgccacttta tgaacgcttc cggcggcggc    1080
gtgacggcat ccggcggcga ggctatcctg caggccgaat ttgttcgcga ctggttccgc    1140
gcctgtaaga agaaggtat tcatacctgt ctcgatacca acggctttgt gcgccgctac    1200
gatccggtta ttgatgaact gctggaggtc accgacctgg tgatgctcga tctcaagc     1258
```

<210> SEQ ID NO 17
<211> LENGTH: 28
<212> TYPE: DNA
<213> ORGANISM: Artificial
<220> FEATURE:
<223> OTHER INFORMATION: primer

<400> SEQUENCE: 17
ccatctgcat cgtatccgct ggcttaat     28

<210> SEQ ID NO 18
<211> LENGTH: 26
<212> TYPE: DNA
<213> ORGANISM: Artificial
<220> FEATURE:
<223> OTHER INFORMATION: primer

<400> SEQUENCE: 18
gctgaagcgg ttgcacatat tacctg     26

<210> SEQ ID NO 19
<211> LENGTH: 30
<212> TYPE: DNA
<213> ORGANISM: Artificial
<220> FEATURE:
<223> OTHER INFORMATION: primer

<400> SEQUENCE: 19
accatcacta agggttgttt caggcagtaa     30

<210> SEQ ID NO 20
<211> LENGTH: 30
<212> TYPE: DNA
<213> ORGANISM: Artificial
<220> FEATURE:
<223> OTHER INFORMATION: primer

<400> SEQUENCE: 20
gctaaaaagg ccccacttgc gtggagcctt     30